(12) United States Patent
Fathman et al.

(10) Patent No.: US 7,964,369 B2
(45) Date of Patent: Jun. 21, 2011

(54) POLYPEPTIDE COMPLEX THAT REGULATES CELL CYCLE AND ANERGY

(75) Inventors: C. Garrison Fathman, Stanford, CA (US); Luis Soares, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 772 days.

(21) Appl. No.: 10/579,049

(22) PCT Filed: Nov. 9, 2004

(86) PCT No.: PCT/US2004/037692
§ 371 (c)(1),
(2), (4) Date: Sep. 18, 2008

(87) PCT Pub. No.: WO2005/046452
PCT Pub. Date: May 26, 2005

(65) Prior Publication Data
US 2009/0012017 A1    Jan. 8, 2009

Related U.S. Application Data

(60) Provisional application No. 60/518,873, filed on Nov. 10, 2003.

(51) Int. Cl.
*G01N 33/53* (2006.01)
*C12Q 1/00* (2006.01)
*C12P 19/34* (2006.01)

(52) U.S. Cl. .......... 435/7.9; 435/4; 435/91.52; 977/886; 424/94.5

(58) Field of Classification Search .................. None
See application file for complete search history.

(56) References Cited

OTHER PUBLICATIONS

Anandasabapathy; et al., "GRAIL: An E3 Ubiquitin Ligase that Inhibits Cytokine Gene Transcription is Expressed in Anergic CD4+T Cells", Immunity, Apr. 2003, 18:535-547.
Balakirev; et al., "Otubains: a new family of cysteine proteases in the ubiquitin pathway", EMBO Reports, Apr. 2003, 4(5):517-522.
Gnesutta; et al., "Cloning and Characterization of Mouse UBPy, a Deubiquitinating Enzyme That Interacts with the Ras Guanine Nucleotide Exchange Factor CDC25Mm/Ras-GRF1" J. Biol. Chem (2001), 276(42):39448-39454.
Kato; et al., "A Deubiquitinating Enzyme UBPY Interacts with the Src Homology 3 Domain of Hrs-binding Protein via a Novel Binding Motif PX(V/I)(D/N) RXXKP"J. Biol. Chem (2000), 275(48):37481-37487.
Nanao; et al., "Crystal structure of human otubain 2", EMBO Reports, Jul. 2004, 5(8):783-788.
Naviglio; et al., "UBPY: a growth-regulated human ubiquitin isopeptidase" The EMBO Journal (1998), 17 (12):3241-3250.
Seroogy; et al., "The Gene Related to Anergy in Lymphocytes, an E3 Ubiquitin Ligase, Is Necessary for Anergy Induction in CD4 T Cells", The Journal of Immunology (2004), 173:79-85.
Soares; et al., "Two isoforms of otubain 1 regulate T cell anergy via GRAIL", Nature Immunology, Jan. 2004, 5 (1):45-54.

*Primary Examiner* — James (Doug) Schultz
(74) *Attorney, Agent, or Firm* — Bozicevic, Field & Francis LLP; Pamela J. Sherwood

(57) ABSTRACT

An active ubiquitin E3 ligase, GRAIL, is crucial in the induction of anergy in cells of the immune system, and in the regulation of cellular proliferation. GRAIL is shown to associate with, and be regulated by Otubain isoforms, including OTUBAIN-1 (DOG, the Destabilizer of GRAIL) and an alternative reading frame splice variant of OTUBAIN-1 (SOG, the Stabilizer of GRAIL). These proteins play opposing roles in the regulation of GRAIL auto-ubiquitination and consequently on its ability to induce anergy and regulate cellular proliferation. DOG serves as an adaptor protein, recruiting the DUB USP8. One major substrate for USP8 is the Ras exchange factor Ras-GRF1, and this protein can be found in a complex with USP8 and GRAIL, which complex is ubiquitinated by GRAIL.

6 Claims, 20 Drawing Sheets

FIG1
A.
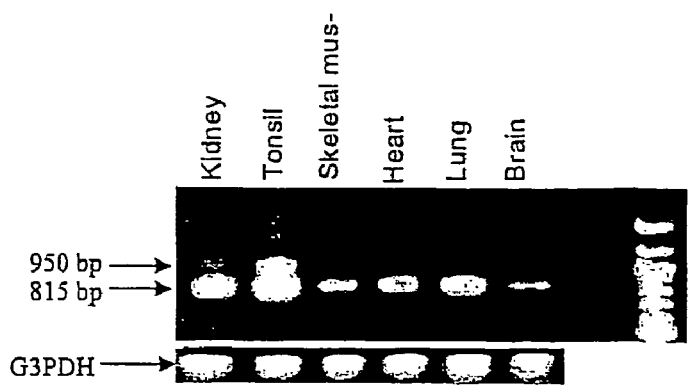
B.
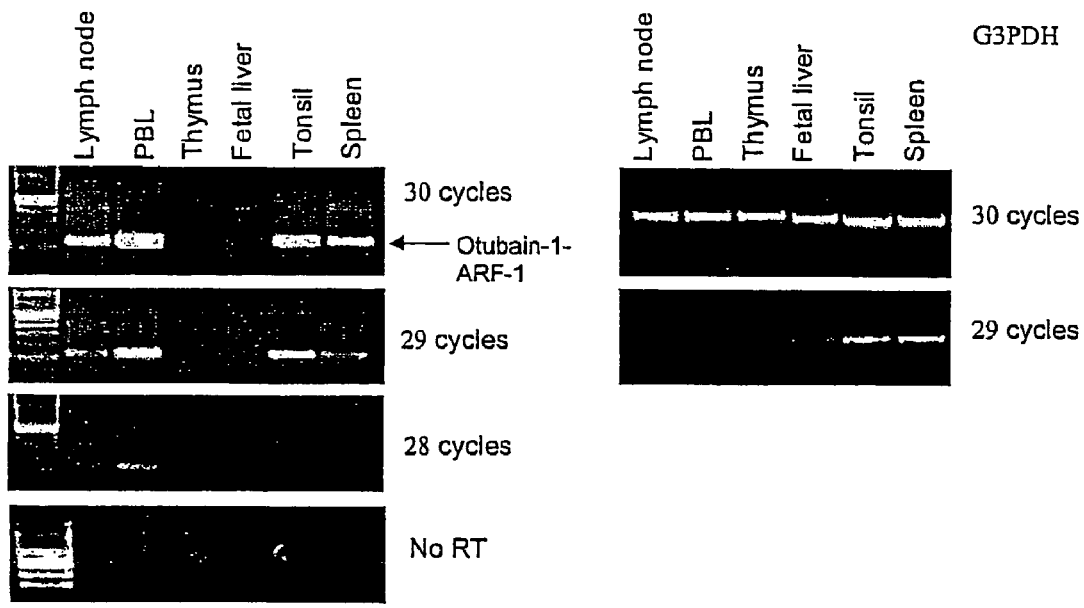
C.
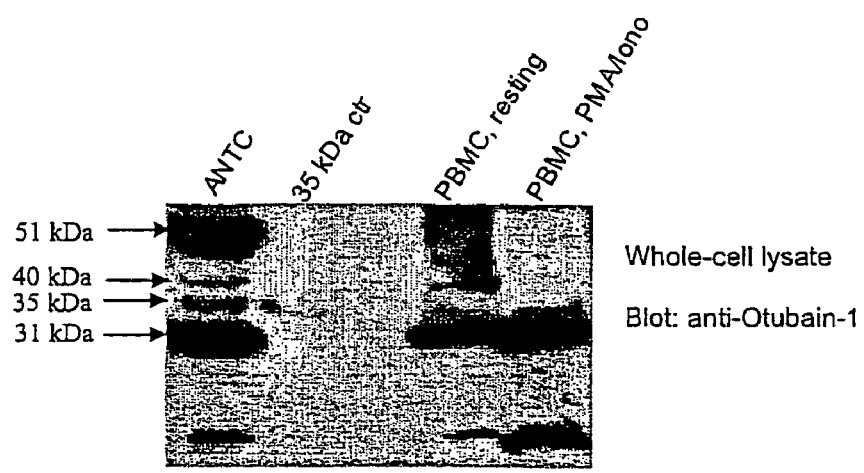

Fig2 c

| | | |
|---|---|---|
| Otb1 | ------MAAEEPQQQKQEPLGSDSEGVNCLAYDEAIMAQQDRIQQ--EIAVQNPLVSER | 51 |
| ARF-1 | MMKPSWLSRTEFSKRLLCRTLWCQS-GWSSRSYTRSMLKMTTSINRRSRTSTKSTRTSAR | 59 |
| | :*.:: .* .:*.* : .::.. *:. .::..: ,.*.* | |
| Otb1 | LELSVLYKEYAEDDNIY--------------------QQKIKDLHKKYSYIR-KTRP-- | 87 |
| ARF-1 | PGLTATVSIGLSDSPTWRHCWMTARSCSGEKGGHWAPRQVGVYLLPGRVGCVSRVSPSF | 119 |
| | :*: . .*. : * * :: .: * | |
| Otb1 | -----DGNCFYRAFGFSHLEALLDDSKEL-------QRFKAVSAKSKEDLVSQGFTEFTI | 135 |
| ARF-1 | PGDGLDSGLARRGSAVSALASGLVEEPMLGPPFHPTPRFKAVSAKSKEDLVSQGFTEFTI | 179 |
| | *.. * .. .* * : . * ************************ | |
| Otb1 | EDFHNTFMDLIEQVERQTSVADLLASFNDQSTSDYLVVYLRLITSGYLQRESKFFEHFIE | 195 |
| ARF1-1 | EDFHNTFMDLIEQVERQTSVADLLASFNDQSTSDYLVVYLRLITSGYLQRESKFFEHFIE | 239 |
| | ************************************************************ | |
| Otb1 | GGRTVKEFCQQEVEPMCKESDHIHIALAQALSVSIQVEYMDRGEGGTTNPHIFPEGSEP | 255 |
| ARF-1 | GGRTVKEFCQQEVEPMCKESDHIHIALAQALSVSIQVEYMDRGEGGTTNPHIFPEGSEP | 299 |
| | ************************************************************ | |
| Otb1 | KVYLLYRPGHYDILYK | 271 |
| ARF-1 | KVYLLYRPGHYDILYK | 315 |

FIG.3
A.
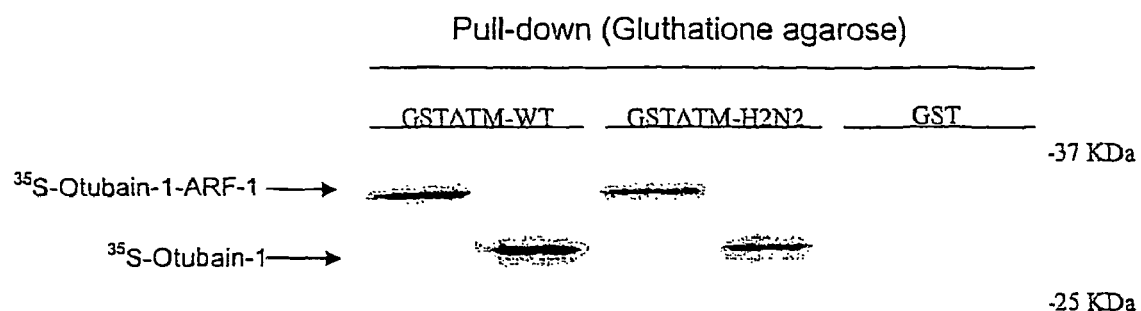
B.
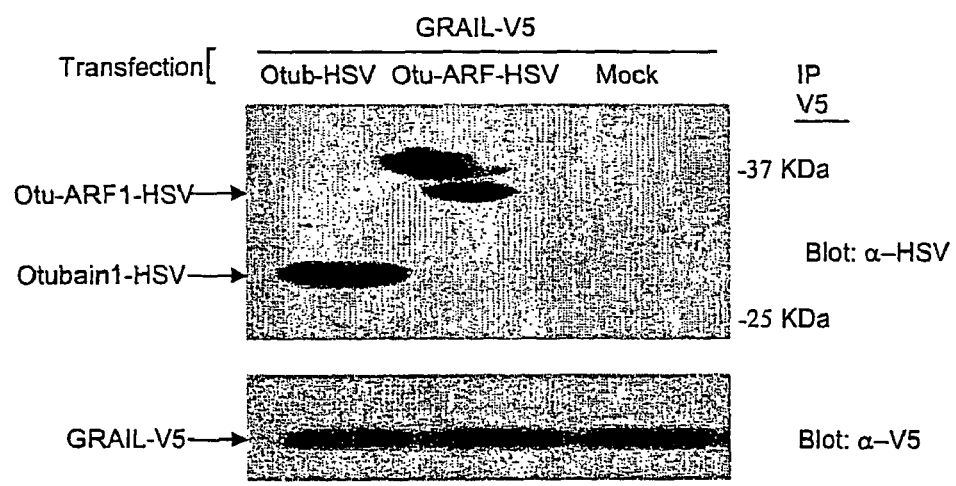

Blot: anti-GRAIL

Total cell lysate input

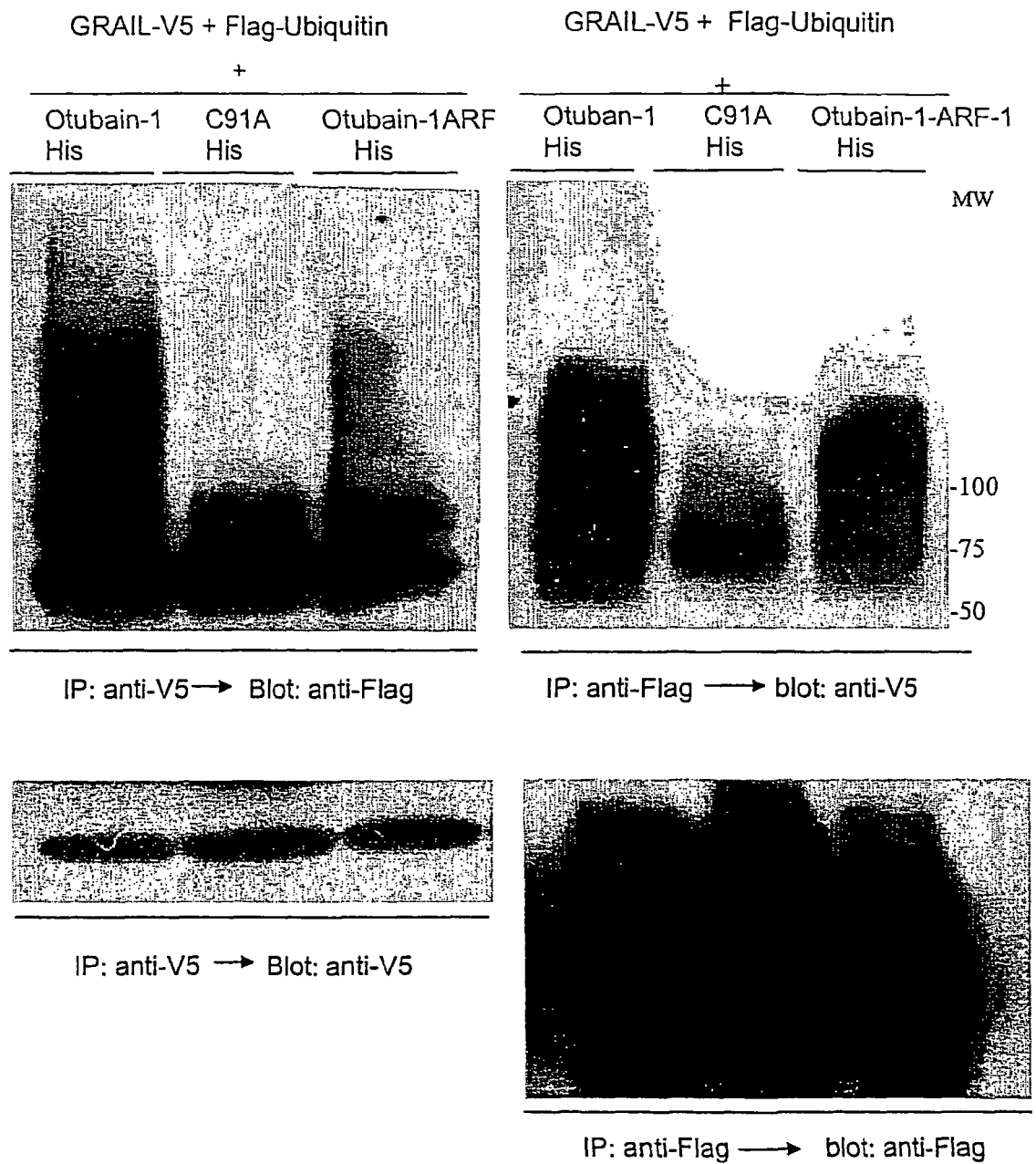

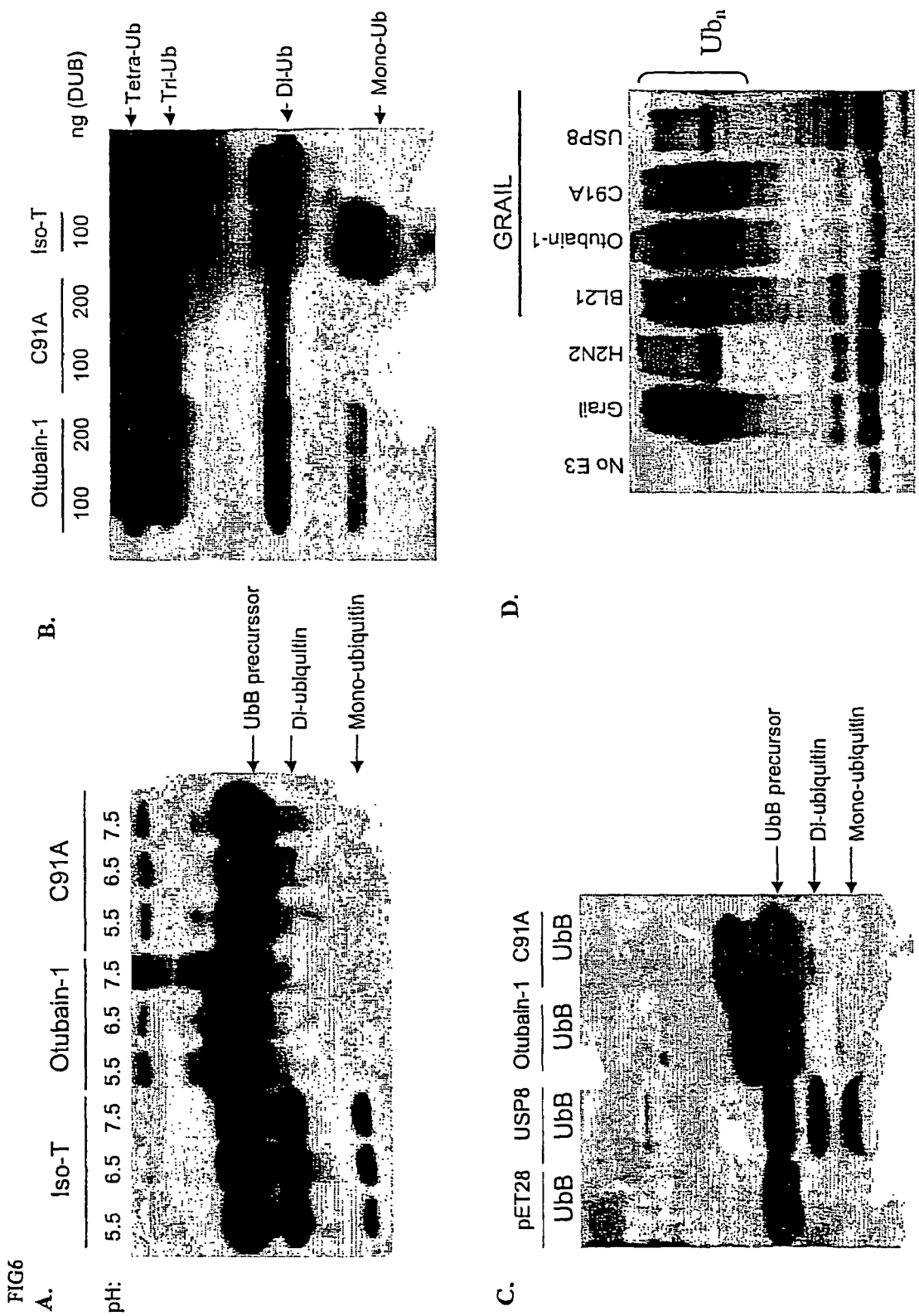

C.

F.

FIG 8
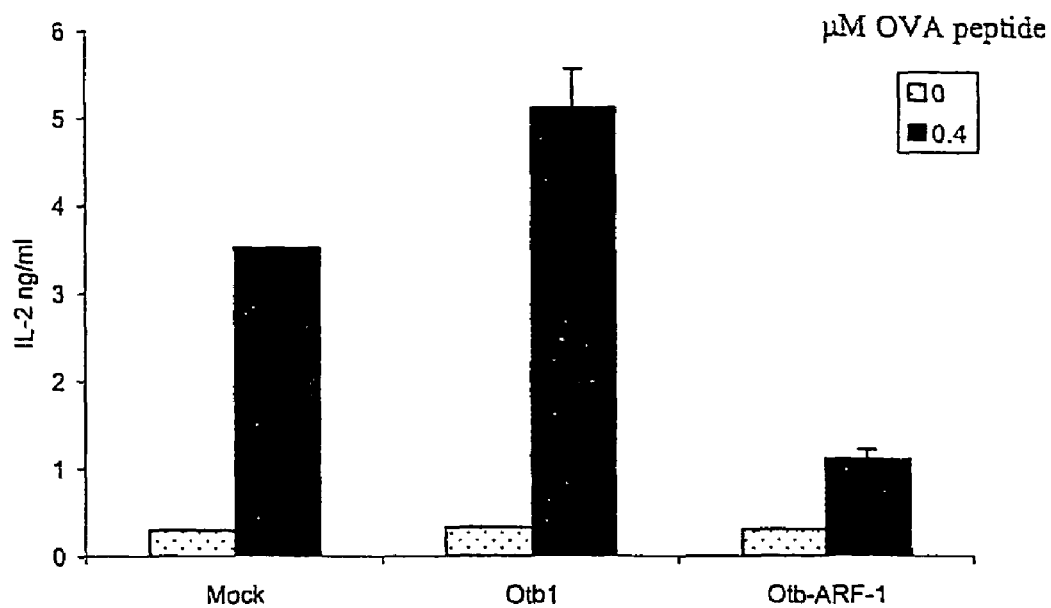
A.
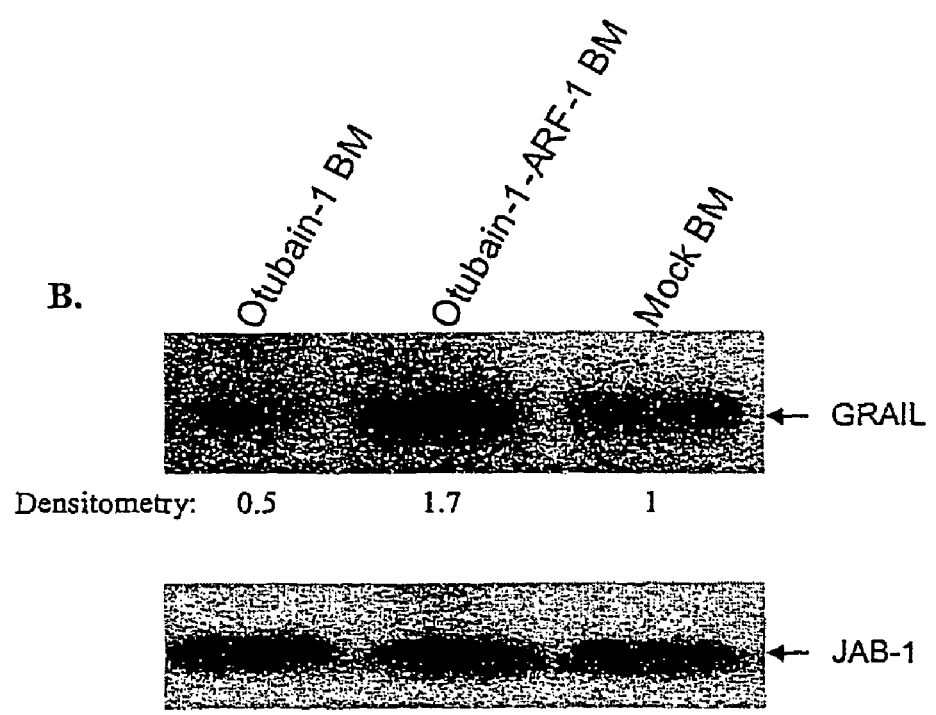
B.

POLYPEPTIDE COMPLEX THAT REGULATES CELL CYCLE AND ANERGY

FEDERALLY-SPONSORED RESEARCH OR DEVELOPMENT

This invention was made with Government support under contract CA065237 awarded by the National Institutes of Health. The Government has certain rights in this invention.

INTRODUCTION

Ubiquitin modification of proteins plays an essential role in diverse cellular pathways, including transport, DNA replication, transcriptional regulation, development and protein degradation. The ubiquitin protein is highly conserved in eukaryotes, and fulfills its function through covalent conjugation to other proteins, a process of high selectivity and efficiency, that relies on equally conserved "ubiquitination machinery." This "machinery" consists of a ubiquitin activating enzyme, E1, which forms a thio-ester with carboxy glycine 76 of ubiquitin; a ubiquitin-conjugating enzyme, E2, that transiently carries the activated ubiquitin; and a ligase (E3) that transfers the activated ubiquitin from E2 to the substrate, promoting the formation of an isopeptide bond between a lysine residue in the substrate and the active c-terminus of ubiquitin. After the addition of the first ubiquitin to the substrate, several other ubiquitins may be added by a similar biochemical reaction A reversal of the ubiquitin reaction, deubiquitination, is carried-out by deubiquitinating enzymes, which belong to the cysteine proteinase family. Recently it was realized that regulation of cellular processes in which ubiquitination plays a role are also deeply dependent on the function of deubiquitinating enzymes. For example, the HAUSP deubiquitinating enzyme deubiquitinates, and therefore favors stabilization, of p53.

E3 ubiquitin ligases utilize one of only two catalytic domains, a HECT domain or a RING finger and are the main determinants of specificity in the ubiquitination reaction. RING E3 ligases in their turn can be classified as single subunit or multi-subunit. Single subunit E3 ligases are in general larger and contain the catalytic RING domain and a substrate-binding domain and in most cases other common protein-protein interaction domain such as coiled-coil regions, or SH2 domains. Functionally, single subunits are able to produce a ubiquitination reaction in vitro when in the presence of an E1 activating enzyme, an E2 conjugating enzyme, ubiquitin and ATP. The GRAIL protein is an example of a single subunit E3 ligase. GRAIL is expected to ubiquitinate a substrate based on its ability to either directly bind to a substrate, or via its association with an adaptor protein, itself bound to a putative substrate.

GRAIL has previously been implicated in the response of T cells to antigen signaling. It is believed that the structural features of the TCR allow it to perceive fine differences in the amino acid sequence of its ligand, and transmit the information through intracellular signaling machinery that is translated into defined patterns of gene expression. TCR signaling can potentially result in proliferation, anergy, or cell death. The outcome of such signals is entirely dependent on complementary signals from other T cell and APC surface receptors. Expression of certain APC surface receptors can be induced in vitro by exposure to inflammatory products such as double-stranded RNA, bacterial lipopolysaccharide, or pro-inflammatory cytokines such as IFN-γ.

Among the downstream signaling events are increased intracellular $Ca^{++}$ levels and activation of the Ras pathway, following recruitment and activation of PLC-γ and the recruitment of the Grb-2-Sos complex, respectively. Once appropriately stimulated, T cells express immediate early genes that promote a transition from G0 into the G1 phase of cell cycle, but not the genes required for DNA synthesis and cell division (phases S and G2/M of the cell cycle). Most of the latter genes are induced only in response to IL-2 binding to the IL-2 receptor. Because activation is a two-step process passage through the mitosis restriction point does not occur until almost 2 days after initial activation. This delay provides time for further modification of the ongoing response, including down-regulation.

Tolerance or clonal anergy, defined as the inability of T cells expressing the appropriate clonotypic TCR to respond to antigen presented in otherwise stimulatory conditions, is one means by which auto-destructive immune responses are avoided. Tolerance is known to be an active process wherein TCR signals are propagated intracellularly and then aborted before IL-2 gene expression is achieved. Most tolerant T cells in mice are believed to have a memory (CD45RB) phenotype and express CD44 (pgp-1), suggesting that they can recirculate and respond to local antigenic challenge. Further, they are comprised primarily of T cells that recognize immunodominant determinants of the antigens to which they are tolerant, suggesting that they might compete with immunocompetent T cells that recognize the same determinants. The molecular basis for tolerance is incompletely understood, but in tolerant cells, TCR signals are unable to activate the proto-oncogene Ras, a small G protein that controls the activation of the major family of mitogenic kinases, the MAP kinases.

Since the induction of T cell anergy requires active signaling and new protein synthesis, it is believed that the establishment of the phenotype results in long lasting changes in the pattern of gene expression when compared to naïve cells or effector T cells. In the T cell compartment, GRAIL is expressed primarily in anergy-induced CD4+ T cells. Forced expression of GRAIL inhibits IL-2 transcription even in the presence of full costimulation, and therefore, mimics anergy.

There is a therapeutic interest in understanding the mechanisms that underlie anergy. Loss of anergy in T cells that recognize self-antigens can lead to autoimmune diseases such as insulin dependent diabetes, rheumatoid arthritis, and multiple sclerosis. In one example of a therapeutic use, the anergy inducing molecule CTLA4Ig has been tested in clinical trials for the treatment of the autoimmune disease psoriasis vulgaris. Conversely, inappropriate anergy may be associated with cancer, where the body fails to mount a response to tumor antigens. The further identification and evaluation of genes involved in the induction and maintenance of anergy and cell cycle regulation, is therefore of great clinical and scientific interest.

Publications

Anandasabapathy et al. (2003) Immunity 18(4):535-47 describe expression of GRAIL in anergic CD4+ T cells. Co-pending U.S. patent application U.S. Ser. No. 09/854,300, herein incorporated by reference, provides a disclosure of the GRAIL protein and its role in anergy.

Ermann et al. (2001) J Immunol. 167(8):4271-5 describe the role of CD4+CD25+ T cells in the facilitation of anergy. Oluwole et al. (2003) Transpl Immunol. 11(3-4):287-93 describe transplant tolerance and CD4+CD25+ regulatory T cells.

The otubain sequence is described by Balakirev (2003) EMBO Rep. 4(5):517-22. The gene is predicted to have, based on genomic sequence, 14 types of transcripts, predicted to encode 14 distinct proteins. It contains 16 confirmed introns, 16 of which are alternative. The transcripts appear to differ by truncation of the N-terminus, truncation of the C-terminus, presence or absence of 6 cassette exons, and common exons with different boundaries, because an internal intron is not always spliced out. Sequences of known transcripts, and partial sequences, may be found, for example, at Genbank, accession numbers AA679586; AA679586, AA679586; AA679586; AV729441; B1770459; AK098029; AA679586; AK000120; BG818896; R84586; AK091830; and BU859734.

The deubiquitinating enzyme UBPY, also known as USP8, is described by Naviglio et al. (1998) EMBO J. 17:3241-3250. Its interaction with Ras-GRF1 is described by Gnesutta et al. (2001) J. Biol. Chem. 276:39448-39454. The interaction of UBPY with Hrs binding protein is described by Kato et al. (2000) J. Biol. Chem. 275:37481-37487.

SUMMARY OF THE INVENTION

It is shown herein that the interaction of the proteins: GRAIL, which is a ubiquitin ligase; otubain splice variants; and the deubiquitinating enzyme USP8, act as regulators in the induction of anergy and regulation of proliferation in cells.

These activities are relevant in autoimmune disease, cancer and other proliferative disorders, and immune function, including the regulation of tolerance. Modulation of the enzymatic activities of these proteins and of the interactions between them provides a basis for regulating immune tolerance; anergy; and cellular proliferation. Determination of the expression of these proteins, particularly determination of the levels of GRAIL polypeptide, which is modulated post-translationally by interactions with DOG; SOG and USP8, are useful diagnostics in determining the proliferative or anergic state of a cell; tissue; organ; tumor; etc. The expression of Otubain isoforms, including DOG and SOG, are also useful in diagnostic applications for detecting cancer and/or autoimmune diseases, using antibodies, mRNA detection, and the like.

In one embodiment of the invention, the biological activity of one or more of GRAIL; SOG; DOG and USP8 is modulated through introduction of genetic coding, anti-sense or RNAi sequences in order to regulate anergy and cellular proliferation. In an other embodiment of the invention the biological activity of one or more of GRAIL; SOG; DOG and USP8 is modulated through introduction of agents that interfere with the interaction between the proteins, where such agents include antibodies, small organic molecules, and the like.

In another embodiment of the invention, screening methods are provided for determining proteins that are substrates of E3 ligases, where such screening methods may be genetic screens, or screens that rely on cell survival in the presence of the substrate.

In another embodiment of the invention, screening methods are provided for determining the biological role of E3 ligases, including GRAIL, in the development of immune tolerance.

In another embodiment of the invention, screening for biologically active agents that alter anergy and cellular proliferation utilizes one or more of GRAIL; DOG; SOG; and USP8, preferably a combination of two or more such proteins. Screening endpoints include stability of GRAIL; ubiquitination levels of GRAIL; and biological activities including induction of anergy.

BRIEF DESCRIPTION OF THE DRAWINGS

FIG. 1: Expression pattern of FLJ20113 (DOG) in human tissues. A) mRNA from diverse human tissues were reverse transcribed and subjected to PC R with primers specific for the FLJ20113 (DOG) coding sequence. A G3PDH amplicon was used as a control. B) mRNA from diverse immune system tissue sources were pre-treated with DNAse and reverse transcribed. The samples were subjected to PCR with primers specific for the alternative spliced form of FLJ20113 with the forward primer annealing to the intronic sequence between exons 4 and 5 as depicted in the inset. G3PDH was used as a control. C) Immunoblot analysis of the expression of, FLJ20113 (DOG) and the alternative spliced forms, including the 35 kDa SOG, with a polyclonal antibody developed against DOG. Lysates shown include those of the ANTC mouse T cell hybridoma and human peripheral blood mononuclear cells either-resting or after 2 hour stimulation with PMA/Ionomycin. The 35 kDa center lane corresponds to in vitro translated SOG (EcoPro T7, Novagen).

FIG. 2C provides an alignment of SEQ ID NO:9 and SEQ ID NO:10.

FIG. 6. DOG has DUB activity toward isolated, branched polyubiquitin chains. A) Recombinant Isopeptidase T, DOG or DOG-C91A (all at 100 ng) were assayed for DUB activity in vitro using recombinant human UbB precursor (a triple head-to-tail fusion of ubiquitin) as a substrate (1 ug). Because DOG has an unusually acidic pI, different pH conditions were tested. Incubations were for 1 hour at 37° C. Reactions were stopped and resolved by SDS-PAGE, transferred to PVDF and immunoblotted with anti-ubiquitin antibody. B) Same reaction as in "A" except that K48-linked branched tetra-ubiquitin was used as a substrate. Our preparation of tetra-ubiquitin had substantial tri and di-ubiquitin contamination; nevertheless, the production of monoubiquitin can be seen to be dependent on the presence of catalytically active DOG or Isopeptidase T. C) E. coli BL21 were co-transformed with the bacterial bicistronic plasmid pACYC Duet (Novagen) carrying a copy of the human UbB gene (containing a His Tag) along with a compatible pET28 plasmid containing DOG, DOG-C91A or USP8. Liquid cultures were induced with IPTG for 3 hours at 34° C. and total cell lysates were prepared, resolved by SDS-PAGE, transferred to PVDF and immunoblotted with anti-His antibody to reveal cleavage of the ubiquitin precursor. D) In vitro ubiquitination reactions with GST-GRAIL (or H2N2) plus E1, E2 ATP and ubiquitin. Stopped reactions were desalted in a microcon spin column and incubated with 100 ng of recombinant DOG, DOG-C91A, USP8 or BL21 lysate for 1 hour at 37° C. and stopped by the addition of Laemli sample buffer. Samples were resolved by SDS-PAGE, transferred to PVDF and immunoblotted with anti-ubiquitin antibody.

FIG. 8. Effects of DOG and SOG on T cell activation (anergy induction) and GRAIL expression, in vivo. (A) DO11.10 bone marrow cells were either mock transduced or transduced with retrovirus encoding DOG or SOG. Cells were sorted for GFP expression prior to infusion into lethally irradiated BALB/c recipients. (A) After engraftment (5-8 weeks), spleen and lymph node tissues were removed and CD4+ T cells purified by positive selection with magnetic beads. CD4+ T cell suspensions were prepared and stimulated with OVA peptide using irradiated splenocytes from normal BABLB/c mice. Supernatants were collected and measured for IL-2 content by ELISA. (B) A fraction of the transduced bone marrow cells was analyzed for GRAIL expression by immunoblot with a GRAIL-specific monoclonal antibody (top panel). The stripped blot was reprobed with anti-Jab-1 antibody as a loading control. Autoradiographs were scanned in a gel densitometer (Bio-Rad) and the density of the bands measured with Quantity one-software (Bio-Rad). A density value of 1 was attributed to the GRAIL band from the mock-transduced BM cells.

DETAILED DESCRIPTION OF THE EMBODIMENTS

Figure 2:
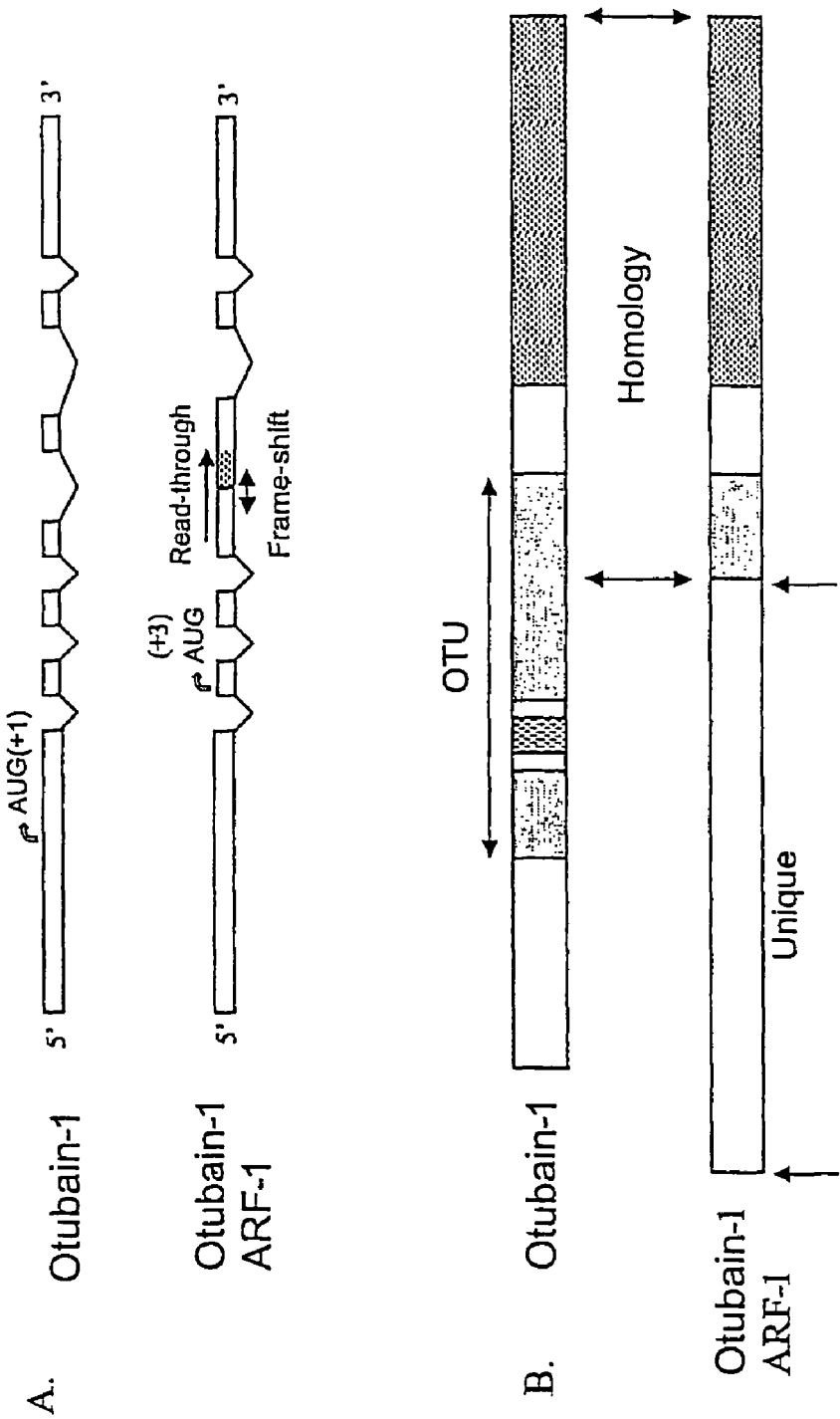
FIGS. 2A-2C: Schematic representation of the DOG/SOG gene and protein. A) The DOG gene contains 7 exons with a translation initiation site in the first exon. The SOG transcript is produced from the same transcription start site but utilizes an AUG codon located on the second exon and in a different reading frame from that of DOG. In addition, the lack of splicing between exons 4 and 5 causes a frame-shift back to the same reading frame as DOG. B,C) Utilization of an AUG in a different frame causes SOG to lose the entire core of the DOG OTU catalytic domain. The frame-shift caused by the read-through of the intron between exons 4 and 5 results in a protein (SOG) that has a c-terminus identical to that of DOG.

An active ubiquitin E3 ligase, GRAIL, is crucial in the induction of anergy in cells of the immune system, and in the regulation of cellular proliferation. GRAIL is shown to associate with, and be regulated by Otubain isoforms, including OTUBAIN-1 (DOG, the Destabilizer of GRAIL) and an alternative reading frame splice variant of OTUBAIN-1 (SOG, the Stabilizer of GRAIL). These proteins play opposing roles in the regulation of GRAIL auto-ubiquitination and consequently on its ability to induce anergy and regulate cellular proliferation. However GRAIL is not a substrate for DOG, nor is DOG a substrate for GRAIL. DOG serves as an adaptor protein in this setting, recruiting the DUB USP8. One major substrate for USP8 is the Ras exchange factor Ras-GRF1, and this protein can be found in a complex with USP8 and GRAIL. The complex is ubiquitinated by GRAIL. The USP8 gene is expressed primarily upon cell activation and is required for cells to enter the S phase of the cell cycle and may serve to stabilize Ras-GRF and prolong Ras signaling. Ras has a crucial role in transducing mitogenic signals, establishing the anergy phenotype, and the development of cancer.

The stabilization of GRAIL, which correlates with decreased levels of ubiquitin on the protein, results in a more anergic state and/or decreased proliferation. The destabilization of GRAIL, which correlates with increased ubiquitin levels, results in a less anergic state and/or increased cellular proliferation.

High levels of DOG expression lead to a correspondent decrease in GRAIL protein levels via increased auto-ubiquitination. Although this is of regulatory nature, loss of control over DOG and or GRAIL expression in some tumors can serve to either accelerate, in the case of DOG up-regulation, or curb tumor development, in the case of GRAIL up-regulation, either directly, at the transcriptional level, or indirectly via down-regulation of DOG. GRAIL may be particularly relevant in conditions where the cell requires an external instruction to grow and divide, e.g. in the initial stages of tumor development, which require autocrine or paracrine growth stimulus, "negotiation" of extracellular matrix contacts, and the promotion of angiogenesis. GRAIL expression was also found to be very low in SLE patients' samples, demonstrating an important element in disease development.

Since E3 ubiquitin ligases promote ubiquitin dependent degradation of their substrates, positive selection genetic screens are provided that rely on ubiquitination as a conditional event for cell survival. This screen can be applied to the identification of substrates for any E3 ligase whose substrates are destined for degradation. Such identification is useful in the evaluation of the pathophysiology or immunotherapy of cancer, autoimmune disease, and transplant rejection.

In yeast two-hybrid assays, a temperature sensitive cdc25 complementation model was used. Because GRAIL is a transmembrane protein localized to endosomes, the cytoplasmic c-terminus of the protein fused to the human GDP/GTP exchange factor Sos was used as bait. The cytoplasmic domain of GRAIL contains the RING domain and a coiled-coil region that is likely to mediate protein interactions. GRAIL interacts, as expected, with E2 conjugating enzymes of the ubc-H5 family and a new E2 conjugating enzyme with a predicted molecular weight of 18 kDa, herein named E2-18 kDa-like ubiquitin conjugating enzyme.

Methods are provided for modulating cellular proliferation and anergy, by regulation of GRAIL function through its interactions with DOG, SOG and USP8. The biological activity of one or more of GRAIL; SOG; DOG and USP8 is modulated through introduction of genetic coding, anti-sense or RNAi sequences, or through the introduction of agents that interfere with the interaction between the proteins, where such agents include antibodies, small organic molecules, and the like. Diagnostic assays assess the expression of these proteins, particularly the levels of GRAIL polypeptide, which is modulated post-translationally.

Polypeptides

Polypeptides include those encoded by native sequences, as well as those encoded by nucleic acids that, by virtue of the degeneracy of the genetic code, are not identical in sequence to the native sequences; and of sequence variants. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a native polypeptide, or a homolog thereof.

As used herein, the term "GRAIL complex" is intended to refer to a complex of GRAIL with an Otubain isoform, including SOG or DOG; where USP8 may also be present. The term "GRAIL complex protein" is used to refer to a member of a GRAIL complex, e.g. an Otubain isoform, SOG, DOG, GRAIL, USP8, Ras-GRF-1; etc.

GRAIL. As used herein, the term "GRAIL" refers to the polypeptide and polynucleotides disclosed in co-pending U.S. patent application U.S. Ser. No. 09/854,300, including variants, homologs and polymorphisms thereof. The GRAIL protein is an E3 ligase, which has the enzymatic activity of ligating ubiquitin to itself, and to its substrates. The presence of high levels of GRAIL protein is indicative of cells that are anergic, or have a low capacity for proliferation.

Figure 3:
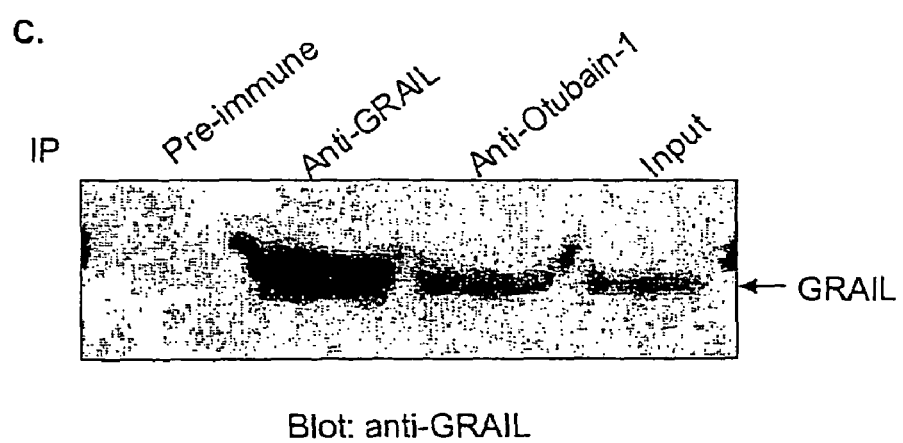
FIGS. 3A-3C. Binding of DOG and SOG to GRAIL does not require an intact RING domain. A) Linearized plasmids encoding either DOG or SOG were used as templates in a combined transcription/translation reaction using a rabbit reticulocyte lysate system (T7-TNT, Promega) and 35S-Met. A portion of the completed reaction was incubated with either recombinant GST-GRAIL fusion protein or GST alone under agitation for 4 hours. Complexes were captured with glutathione-agarose beads, washed several times and eluted with reduced glutathione. Eluted proteins were subjected to electrophoresis and the dried gel exposed to film. B) HEK 293 cells were co-transfected with plasmids coding for GRAIL tagged with V5 and either DOG or SOG, tagged with HSV. GRAIL was immunoprecipitated with anti-V5 antibody and the immunocomplexes were resolved by electrophoresis and transferred to PVDF membranes. Immunoblot was carried-out with anti-HSV and anti-V5 antibodies. C) Liver tissue extracts (5 mg) were immunoprecipitated with polyclonal antibodies to either GRAIL or DOG. A pre-immune rabbit antiserum was used as control. Immunoprecipitates were resolved by SDS-PAGE, transferred to PVDF and immunoblotted with a GRAIL-specific monoclonal antibody.

Otubain Isoforms. The Otubain gene is differentially spliced to give rise to a number of distinct isoforms, which act as regulators of GRAIL, and therefore of anergy and cellular proliferation. The genetic sequences of human SOG and DOG are provided herewith in FIG. 3.

SOG is encoded by an mRNA of about 950 bp, giving rise to a protein of about 35 KDa. The DOG transcript is 815 bp, encoding a 31 KDa protein. The two isoforms differ by an additional 210 bp of coding sequence in the central region of the mRNA. DOG is a ubiquitin specific protease with specificity toward isolated branched polyubiquitin chains, and is widely expressed, whereas SOG is preferentially expressed in secondary lymphoid tissues. The shorter isoform cDNA and the larger isoform to a 35 KDa protein. Both DOG and SOG have identical c-terminal 140 amino acids, including the GRAIL binding domain. However, SOG lacks two of the three amino acids (Asp and Cys) that compose the signature OTU cysteine proteinase catalytic core of the original OTU-BAIN-1, and retains only the C-terminal flanking region of the OTU domain, and therefore lacks the catalytic activity of DOG.

USP8. As used herein, USP8 is a deubiquitinating enzyme. The human sequence may be accessed at Genbank, accession no. D29956. The sequence of USP8 displays the typical hallmarks of the UBP family of de-ubiquitinating enzymes, including the so called histidine and cysteine boxes. There is evidence that it is a phosphoprotein. USP8 can hydrolyze ubiquitin-isopeptide bonds, and linear ubiquitin chains. The protein product appears as a doublet of approximately 130 KDa. Expression is reduced in growth arrested or G0 cells, and increased in proliferating cells.

Compound Screening

Compound screening may be performed using a GRAIL protein complex, e.g. in combination with a source of ubiquitin, a substrate for ubiquitination, energy source, and the like, a genetically altered cell or animal, or one or more purified GRAIL complex proteins. One can identify ligands or substrates that bind to, stabilize, destabilize, inhibit, or potentiate the activity of the GRAIL complex.

Transgenic animals or cells; or animals comprising a graft of such cells are also used in compound screening. Transgenic animals may be made through homologous recombination, where the normal locus is altered. Alternatively, a nucleic acid construct is randomly integrated into the genome. Vectors for stable integration include plasmids, retroviruses and other animal viruses, YACs, and the like. A series of small deletions and/or substitutions may be made in the coding sequence to determine the role of different exons in ligase activity, anergy, signal transduction, etc. Specific constructs of interest include antisense sequences that block expression of the targeted gene and expression of dominant negative mutations. A detectable marker, such as lac Z may be introduced into the locus of interest, where up-regulation of expression will result in an easily detected change in phenotype. One may also provide for expression of the target gene or variants thereof in cells or tissues where it is not normally expressed or at abnormal times of development. By providing expression of the target protein in cells in which it is not normally produced, one can induce changes in cell behavior.

In one embodiment of the invention, the genetically modified cell comprises an integrated copy of a vector, e.g. a retroviral or lentiviral vector; where GRAIL or another GRAIL complex protein is operably linked to an inducible promoter. Cells of interest for evaluation include, inter alia, hematopoietic cells.

Compound screening identifies agents that modulate the function of protein in the GRAIL complex. Of particular interest are screening assays for agents that have a low toxicity for human cells. A wide variety of assays may be used for this purpose, including in vitro phosphorylation assays, electrophoretic mobility shift assays, immunoassays for protein binding, and the like. Knowledge of the 3-dimensional structure of the encoded protein, derived from crystallization of purified recombinant protein, could lead to the rational design or the virtual screening of small drugs that specifically inhibit activity. These drugs may be directed at specific domains.

The term "agent" as used herein describes any molecule, e.g. protein or pharmaceutical, usually with the capability of inhibiting, potentiating, stabilizing, destabilizing, interfering with binding, etc. of, or between, proteins of the GRAIL complex, e.g. to alter levels of ubiquitination of GRAIL and GRAIL substrates, to increase or decrease cellular proliferation; to induce anergy; and the like. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

In one embodiment of the invention, the candidate agent of interest is a peptide and derivatives thereof, e.g. high affinity peptides or peptidomimetic substrates for proteins of the GRAIL complex, particularly a substrate modified to act as an inhibitor. Such peptides may be resistant toward endo- and exo-proteolysis by gastric, pancreatic and small intestinal enzymes. Therefore selective inhibitors can be prepared by substituting serine mimetics that act as mechanism based inhibitors.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Generally, peptide agents encompassed by the methods provided herein range in size from about 3 amino acids to about 100 amino acids, with peptides ranging from about 3 to about 25 being typical and with from about 3 to about 12 being more typical. Peptide agents can be synthesized by standard chemical methods known in the art (see, e.g., Hunkapiller et al., *Nature* 310:105-11, 1984; Stewart and Young, *Solid Phase Peptide Synthesis*, 2$^{nd}$ Ed., Pierce Chemical Co., Rockford, Ill., (1984)), such as, for example, an automated peptide synthesizer. In addition, such peptides can be produced by translation from a vector having a nucleic acid sequence encoding the peptide using methods known in the art (see, e.g., Sambrook et al., *Molecular Cloning, A Laboratory Manual*, 3rd ed., Cold Spring Harbor Publish., Cold Spring Harbor, N.Y. (2001); Ausubel et al., *Current Protocols in Molecular Biology*, 4th ed., John Wiley and Sons, New York (1999); which are incorporated by reference herein).

Peptide libraries can be constructed from natural or synthetic amino acids. For example, a population of synthetic peptides representing all possible amino acid sequences of length N (where N is a positive integer), or a subset of all possible sequences, can comprise the peptide library. Such peptides can be synthesized by standard chemical methods known in the art (see, e.g., Hunkapiller et al., *Nature* 310:105-11, 1984; Stewart and Young, *Solid Phase Peptide Synthesis*, $2^{nd}$ Ed., Pierce Chemical Co., Rockford, Ill., (1984)), such as, for example, an automated peptide synthesizer. Nonclassical amino acids or chemical amino acid analogs can be used in substitution of or in addition into the classical amino acids. Non-classical amino acids include but are not limited to the D-isomers of the common amino acids, α-amino isobutyric acid, 4-aminobutyric acid, 2-amino butyric acid, γ-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to proteins in the GRAIL complex, as at least some of the compounds so identified are likely to be active. The binding assays usually involve contacting GRAIL complex with one or more test compounds and allowing sufficient time for the protein and test compounds to form a binding complex. Any binding complexes formed can be detected using any of a number of established analytical techniques including surface plasmon resonance and LC-MS.

Certain screening methods involve screening for a compound that modulates the stability of GRAIL. Such methods may involve conducting cell-based assays in which test compounds are contacted with one or more cells expressing GRAIL complex and then detecting an increase in protein levels. Some assays are performed with lymphocytes that express endogenous GRAIL complex genes. Other expression assays are conducted with cells that express an exogenous GRAIL complex gene or cells that express a reporter gene under the control of the GRAIL complex promoter.

The level of expression or activity can be compared to a baseline value. As indicated above, the baseline value can be a value for a control sample or a statistical value that is representative of expression levels for a control population. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal that serves as a model for human disease, e.g. in development of tolerance, autoimmune disease include SLE, cancer etc., and then determining the alteration of expression levels in vivo. The animal models utilized in validation studies generally are mammals. Specific examples of suitable animals include, but are not limited to, primates, mice, and rats.

Active test agents identified by the screening methods described herein that inhibit GRAIL complex activity and/or alter induction of immune tolerance, autoimmune disease, cellular proliferation, etc. can serve as lead compounds for the synthesis of analog compounds. Typically, the analog compounds are synthesized to have an electronic configuration and a molecular conformation similar to that of the lead compound.

Alternative compounds for inhibition of GRAIL complex include the administration of interference RNA (RNAi), or of antisense oligonucleotides. In this approach, a molecule of double-stranded RNA specific to a gene of the GRAIL complex, e.g. otubain isoform; USP8; GRAIL; etc., is used. Double-stranded RNA is introduced into cells expressing a GRAIL complex, in order to inhibit expression of the gene. The dsRNA is selected to have substantial identity with the target GRAIL complex protein sequence. Because only substantial sequence similarity between the target sequence and the dsRNA is necessary, sequence variations between these two species arising from genetic mutations, evolutionary divergence and polymorphisms can be tolerated. Moreover, the dsRNA can include various modified or nucleotide analogs. Usually the dsRNA consists of two separate complementary RNA strands. However, in some instances, the dsRNA may be formed by a single strand of RNA that is self-complementary, such that the strand loops back upon itself to form a hairpin loop. Regardless of form, RNA duplex formation can occur inside or outside of a cell.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis.

The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes 1 and 11 (D. N. Glover, Ed., 1985); and Oligonucleotide Synthesis (M. J. Gait, Ed., 1984, each of which is incorporated herein by reference in its entirety).

Once the dsRNA has been formed, it is introduced into a cell. A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

Animal Model for Function of the Grail Complex

Animal models are useful in evaluating functional gene expression in the immune system. One animal model of interest comprises a bone marrow chimera, where immune cells from a donor animal are used to reconstitute the immune system of a syngeneic recipient, which may have a compromised immune system, e.g. as a result of irradiation, or may have an intact immune system. Donor cells may be bone marrow or cell fractions derived therefrom, particularly hematopoietic stem cells, long-term multipotent progenitors, lymphoid progenitor cells, and the like. A preferred source of donor cells are cells from a transgenic animal having a defined T cell specificity, where the T cells have a single antigenic specificity, usually a specificity for a non-native antigen. Examples of such transgenic animals include D011.10 TCR transgenic mice, which are reactive towards $OVA_{323-339}$ peptide.

The donor cells are transduced with a vector, e.g. a retroviral vector, lentiviral vector, etc., expressing a biologically active protein of the GRAIL complex, e.g. otubain splice variants, GRAIL, USP8, etc.; or as controls, inactive proteins, e.g. the E3 ligase-inactive form of GRAIL (H2N2). Preferably a marker gene, e.g. green fluorescent protein (GFP) and variants thereof, drug resistance marker, etc. is located downstream of an IRES sequence and the gene of interest, where expression of the marker gene is used to track expression of the GRAIL complex gene. The GRAIL complex sequence may be constitutively expressed, inducibly expressed, or regulated by its native promoter elements.

Cells, including sorted population of T cells, tissues of interest, lymph node cells, etc., are obtained from the recipient animal for determination of biological function, e.g. by exposure to the cognate antigen for the TCR. Inducible promoter expression can be tested by contacting the cells with the inducing agent. The detectable marker can be used to identify donor cells expressing the gene of interest; and can also be used in FACS sorting to isolate cells expressing the gene of interest, e.g. to determine the expression levels of DOG and SOG in cells expressing GRAIL; and vice versa.

Alternatively, the cells can be tested in vivo, by exposing the animal to the cognate antigen. Following immunization, tissues, e.g. lymph node (cervical, axillary, brachial, and inguinal), spleen, etc. may be evaluated by determining proliferation with an in vitro assay. The expression of a dominant negative mutation of GRAIL, for example, has been found to block the ability of these cells to be anergized. Constitutive DOG expression in naïve CD4+ T cells resulted in increased IL-2 production, while expression of SOG resulted in almost no IL-2 production. These data have shown that the balance of DOG and SOG expression in T cells is an important factor regulating GRAIL levels and therefore the outcome of immune responses in secondary lymphoid organs.

Screening Methods for E3 Ligase Substrates

E3 ubiquitin ligases promote ubiquitin dependent degradation of their substrates, thus a positive selection genetic screen that relies on E3-mediated ubiquitination as a conditional event for cell survival will identify the substrate(s) of the enzyme.

There is no conventional method for the determination of RING finger E3 ligase substrates. Proteomic efforts are hampered by the fact that ubiquitination is a "ubiquitous" reaction in the cell, resulting in very high background levels. Genetic screens in association with biochemical data have historically allowed powerful insights into the inner workings of cellular physiology. Since E3 ubiquitin ligases promote ubiquitin dependent degradation of their substrates, a positive selection genetic screen is constructed that relies on E3-mediated ubiquitination as a conditional event for cell survival. This screen is applicable to the identification of substrates for any E3 ligase whose substrates are destined for degradation.

A positive selection system is based on E3-mediated ubiquitination and target degradation as a conditional event for cell survival under drug selection. The system is based on an enzyme, deficient cell line, for which deficiency there exists a negative selection, preferably a positive and negative selection, e.g. thymidine kinase. The cell is genetically modified to comprise a composite vector containing an inducible promoter construct with a coding sequence of an E3 ligase, operably linked so that it can be induced with the appropriate agent, e.g. tetracycline, ecdysone, etc. The construct also carries a drug selection cassette.

A copy of an open reading frame encoding the enzyme is cloned into an expression vector, where the sequence is fused at its C-terminus to a library of potential substrate sequences, e.g. a cDNA library, defined peptide library, etc. The vector comprising the enzyme sequence and candidate substrate sequences is introduced into the inducible E3 expressing cell. Where the vector is a viral vector, the vector may be appropriately packaged for higher efficiency. Where the enzyme is thymidine kinase, cells containing an integrated copy of the vector can be selected on HAT medium, since the parental line is TK negative. Surviving cells are then treated to induce E3 expression, followed by administration of a toxic TK substrate prodrug, e.g. acyclovir, gancyclovir, etc. If a substrate is correctly expressed in frame with the enzyme, E3 mediated ubiquitination of the fusion protein will induce its degradation and therefore promote cell survival in the presence of the pro-drug.

The insert conferring resistance to the prodrug can be is rescued from the vector by a variety of methods, e.g. PCR amplification using specific primers, plaque isolation, etc., and characterized according to sequence, expression, etc.

Substrates may be confirmed by biochemical means, e.g. by co-transfection of coding sequence for the E3 ligase and the candidate substrate, and performing an immunoprecipitation to determine if the proteins interact. For example, two, three or more coding sequences are transfected into a cell, and the levels of the substrate compound monitored, where the levels are decreased in the presence of active ubiquitination. Alternatively, two hybrid analysis is performed, particularly in bacterial cells, which lack an active ubiquitination pathway.

Pharmaceutical Compositions

Compounds identified by the screening methods described above and analogs thereof can serve as the active ingredient in pharmaceutical compositions formulated for the treatment of various hyperproliferative disorders, including lack of immune tolerance, autoimmune disease, cancer, etc. The compositions can also include various other agents to enhance delivery and efficacy. For instance, compositions can include agents capable of increasing the bioavailability of the compound. The compositions can also include various agents to enhance delivery and stability of the active ingredients.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese) and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules, which consist of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Therapeutic/Prophylactic Treatment Methods

Agents that modulate activity of the GRAIL complex provide a point of therapeutic or prophylactic intervention. Numerous agents are useful in modulating this activity, including agents that directly modulate expression, e.g. expression vectors, antisense specific for the targeted kinase; and agents that act on the protein, e.g. specific antibodies and analogs thereof, small organic molecules that block catalytic activity, etc. Agents may be administered to patients suffering from autoimmune or immune tolerance disorders, hyperproliferative conditions, etc.

Animals of interest for therapy include human patients, animal models for disease, veterinary purposes, and the like, and will generally be mammals, e.g. primates, equines, felines, rodents, canines, etc.

As used herein, the term "treating" is used to refer to both prevention of disease, and treatment of pre-existing conditions. The prevention of proliferation is accomplished by administration of the compounds prior to development of overt disease, e.g., to prevent the development of autoimmune disease; the regrowth of tumors; prevent metastatic growth; diminish graft rejection or autoimmune disease, etc. Alternatively the compounds are used to treat ongoing disease, by stabilizing or improving the clinical symptoms of the patient.

The susceptibility of a particular cell or tissue to treatment with the subject compounds may be determined by in vitro testing. Typically a culture of the cell is combined with a subject compound at varying concentrations for a period of time sufficient to allow the active agents to induce anergy, usually between about one hour and one week. For in vitro testing, cultured cells from a biopsy sample may be used. The cycling cells left after treatment are then counted.

Antisense or RNAi sequences may be administered to inhibit expression. Other inhibitors are identified by screening for biological activity in a functional assay, e.g. in vitro or in vivo ubiquitin ligase activity, polypeptide stability, etc.

Expression vectors may be used to introduce a polynucleotide sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least several days to several weeks.

The vector may be introduced into tissues or host cells by any number of routes, including viral infection, microinjection, or fusion of vesicles. Jet injection may also be used for intramuscular administration, as described by Furth et al. (1992) Anal Biochem 205:365-368. The DNA may be coated onto gold microparticles, and delivered intradermally by a particle bombardment device, or "gene gun" as described in the literature (see, for example, Tang et al. (1992) Nature 356:152-154), where gold micro projectiles are coated with the protein or DNA, then bombarded into skin cells.

Methods can be designed to selectively deliver nucleic acids to certain cells. Examples of such cells include T cells, cancer cells, etc. Certain treatment methods are designed to selectively express an expression vector to lymphocytes and/or target the nucleic acid for delivery to lymphocytes. One technique for achieving selective expression in cells of interest is to operably link the coding sequence to a promoter that is primarily active in nerve cells. Examples of such promoters include, but are not limited to, the immunoglobulin or T cell receptor promoter regions. Alternatively, or in addition, the nucleic acid can be administered with an agent that targets the nucleic acid. For instance, the nucleic acid can be administered with an antibody that specifically binds to a cell-surface antigen on the nerve cells or a ligand for a receptor on neuronal cells.

When liposomes are utilized, substrates that bind to a cell-surface membrane protein associated with endocytosis can be attached to the liposome to target the liposome to nerve cells and to facilitate uptake. Examples of proteins that can be attached include capsid proteins or fragments thereof that bind to cells, antibodies that specifically bind to cell-surface proteins on cells of interest that undergo internalization in cycling and proteins that target intracellular localizations within cells of interest (see, e.g., Wu et al. (1987) J. Biol. Chem. 262:4429-4432; and Wagner, et al. (1990) Proc. Natl. Acad. Sci. USA 87:3410-3414). Gene marking and gene therapy protocols are reviewed by Anderson et al., (1992) Science 256:808-813.

The dose will vary depending on the specific compound utilized, specific disorder, patient status, etc. For treatment of tumors, typically a therapeutic dose will be sufficient to substantially decrease the proliferation of the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body. For treatment of autoimmune disease, therapeutic effects may be measured by a decrease in immune responsiveness against the target antigen; or decrease in patient symptoms, e.g. the presence of antinuclear antibodies in SLE; and the like.

There are many disorders associated with a dysregulation of cellular proliferation. The conditions of interest include, but are not limited to, the following conditions.

Diseases where there is hyperproliferation and tissue remodelling or repair of reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to modulate cell death (apoptosis) and activate angiogenesis to produce a tumor neovasculature.

Tumors of interest for treatment include carcinomas, e.g., colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies; e.g., neuroblastoma, gliomas, etc.; hematological malignancies, e.g., childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Other hyperproliferative diseases of interest relate to epidermal hyperproliferation, tissue, remodeling and repair. For example, the chronic skin inflammation of psoriasis is associated with hyperplastic epidermal keratinocytes as well as infiltrating mononuclear cells, including $CD4^+$ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

Systemic lupus erythematosus (SLE) is an autoimmune disease characterized by polyclonal B cell activation, which results in a variety of anti-protein and non-protein autoantibodies (see Kotzin et al. (1996) Cell 85:303-306 for a review of the disease). These autoantibodies form immune complexes that deposit in multiple organ systems, causing tissue damage. SLE is a difficult disease to study, having a variable disease course characterized by exacerbations and remissions. For example, some patients may demonstrate predominantly skin rash and joint pain, show spontaneous remissions, and require little medication. The other end of the spectrum includes patients who demonstrate severe and progressive kidney involvement (glomerulonephritis) that requires therapy with high doses of steroids and cytotoxic drugs such as cyclophosphamide.

It appears that multiple factors contribute to the development of SLE. Several genetic loci may contribute to susceptibility, including the histocompatibility antigens HLA-DR2 and HLA-DR3. The polygenic nature of this genetic predisposition, as well as the contribution of environmental factors, is suggested by a moderate concordance rate for identical twins, of between 25 and 60%.

Disease manifestations result from recurrent vascular injury due to immune complex deposition, leukothrombosis, or thrombosis. Additionally, cytotoxic antibodies can mediate autoimmune hemolytic anemia and thrombocytopenia, while antibodies to specific cellular antigens can disrupt cellular function. An example of the latter is the association between anti-neuronal antibodies and neuropsychiatric SLE.

Nucleic Acids

The sequences of proteins and encoding nucleic acids of the GRAIL complex find use in diagnostic and prognostic methods, for the recombinant production of the encoded polypeptides, and the like. The sequences of interest include both a double stranded nucleic acid sequence, and the encoded polypeptide sequence. The nucleic acids of the invention include nucleic acids having a high degree of sequence similarity or sequence identity to a GRAIL complex gene sequence. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to one of the sequences provided in Table 1 under stringent hybridization conditions. Further specific guidance regarding the preparation of nucleic acids is provided by Fleury et al. (1997) Nature Genetics 15:269-272; Tartaglia et al., PCT Publication No. WO 96/05861; and Chen et al., PCT Publication No. WO 00/06087, each of which is incorporated herein in its entirety. Included are homologous genes, which may include mouse, human, rat, etc. forms of a gene or protein.

GRAIL complex gene sequences may be obtained using various methods well known to those skilled in the art, including but not limited to the use of appropriate probes to detect the genes within an appropriate cDNA or genomic DNA library, antibody screening of expression libraries to detect cloned DNA fragments with shared structural features, direct chemical synthesis, and amplification protocols. Cloning methods are described in Berger and Kimmel, Guide to Molecular Cloning Techniques, Methods in Enzymology, 152, Academic Press, Inc. San Diego, Calif.; Sambrook, et al. (1989) Molecular Cloning—A Laboratory Manual (2nd ed) Vols. 1-3, Cold Spring Harbor Laboratory, Cold Spring Harbor Press, NY; and Current Protocols (1994), a joint venture between Greene Publishing Associates, Inc. and John Wiley and Sons, Inc.

The sequence obtained from clones containing partial coding sequences or non-coding sequences can be used to obtain the entire coding region by using the RACE method (Chenchik et al. (1995) CLONTECHniques (X) 1: 5-8). Oligonucleotides can be designed based on the sequence obtained from the partial clone that can amplify a reverse transcribed mRNA encoding the entire coding sequence. Alternatively, probes can be used to screen cDNA libraries prepared from an appropriate cell or cell line in which the gene is transcribed. Once the target nucleic acid is identified, it can be isolated and cloned using well-known amplification techniques. Such techniques include, the polymerase chain reaction (PCR) the ligase chain reaction (LCR), Qβ-replicase amplification, the self-sustained sequence replication system (SSR) and the transcription based amplification system (TAS). Such methods include, those described, for example, in U.S. Pat. No. 4,683,202 to Mullis et al.; PCR Protocols A Guide to Methods and Applications (Innis et al. eds) Academic Press Inc. San Diego, Calif. (1990); Kwoh et al. (1989) Proc. Natl. Acad. Sci. USA 86: 1173; Guatelli et al. (1990) Proc. Natl. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4: 560; and Barringer et al., (1990) Gene 89: 117.

As an alternative to cloning a nucleic acid, a suitable nucleic acid can be chemically synthesized. Direct chemical synthesis methods include, for example, the phosphotriester method of Narang et al. (1979) Meth. Enzymol. 68: 90-99; the phosphodiester method of Brown et al. (1979) Meth. Enzymol. 68:109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids can be cDNAs or genomic DNAs, as well as fragments thereof. The term "cDNA" as used herein is intended to include all nucleic acids that share the arrangement of sequence elements found in native mature mRNA species, where sequence elements are exons and 3' and 5' non-coding regions, and includes, e.g., the isoforms of otubain. Normally mRNA species have contiguous exons, with the intervening introns, when present, being removed by nuclear RNA splicing, to create a continuous open reading frame encoding a polypeptide of the invention.

Genomic sequences of interest comprise the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA flanking the coding region, either 3' or 5', or internal regulatory sequences as sometimes found in introns, contains sequences required for proper tissue, stage-specific, or disease-state specific expression.

Specific probes can be generated using the disclosed nucleic acid sequences. The probes are preferably at least about 18 nt, 25 nt, 50 nt or more of the corresponding contiguous sequence, and are usually less than about 2, 1, or 0.5 kb in length. Preferably, probes are designed based on a contiguous sequence that remains unmasked following application of a masking program for masking low complexity, e.g. BLASTX. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Antisense and RNAi molecules can be used to down-regulate expression in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Polypeptides

Polypeptides of the GRAIL complex are of interest for screening methods, as reagents to raise antibodies, as therapeutics, and the like. Such polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as a native polypeptide.

The polypeptides may be produced by recombinant DNA technology using techniques well known in the art. Methods that are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Typically, the coding sequence is placed under the control of a promoter that is functional in the desired host cell to produce relatively large quantities of the gene product. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, E. coli, other bacterial hosts, yeast, and various higher eukaryotic cells such as the COS, CHO and HeLa cells lines and myeloma cell lines.

In mammalian host cells, a number of viral-based expression systems may be used, including retrovirus, lentivirus, adenovirus, adeno associated virus, and the like. In cases where an adenovirus is used as an expression vector, the coding sequence of interest can be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a GRAIL complex protein in infected hosts.

Specific initiation signals may also be required for efficient translation of the genes. These signals include the ATG initiation codon and adjacent sequences. In cases where a complete gene, including its own initiation codon and adjacent sequences, is inserted into the appropriate expression vector, no additional translational control signals may be needed. However, in cases where only a portion of the gene coding sequence is inserted, exogenous translational control signals must be provided. These exogenous translational control signals and initiation codons can be of a variety of origins, both natural and synthetic. The efficiency of expression may be enhanced by the inclusion of appropriate transcription enhancer elements, transcription terminators, etc.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, production of recombinant proteins, stable expression is preferred. For example, cell lines that stably express GRAIL complex may be engineered. Rather than using expression vectors that contain viral origins of replication, host cells can be transformed with DNA controlled by appropriate expression control elements, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the target protein. Such engineered cell lines may be particularly useful in screening and evaluation of compounds that affect the endogenous activity of the differentially expressed or pathway gene protein. A number of selection systems may be used, including but not limited to the herpes simplex virus thymidine kinase, hypoxanthine-guanine phosphoribosyltransferase, and adenine phosphoribosyltransferase genes. Antimetabolite resistance can be used as the basis of selection for dhfr, which confers resistance to methotrexate; gpt, which confers resistance to mycophenolic acid; neo, which confers resistance to the aminoglycoside G418; and hygro, which confers resistance to hygromycin.

The polypeptide may be labeled, either directly or indirectly. Any of a variety of suitable labeling systems may be used, including but not limited to, radioisotopes such as $^{125}$I; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by an Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

As an option to recombinant methods, polypeptides and oligopeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of a GRAIL complex protein can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993).

Diagnostic and Prognostic Methods

The interaction between GRAIL, DOG and SOG during the development of T cell tolerance, loss of anergy (tolerance)

and during regulation of proliferation indicate a use as a marker for diagnosing individuals that have cancer, autoimmune disease, are at risk of such diseases, and the like. Diagnostic methods include detection of specific markers correlated with specific stages in the pathological processes leading to hyperproliferation, loss of immune tolerance. Knowledge of the progression stage can be the basis for more accurate assessment of the most appropriate treatment and most appropriate administration of therapeutics. Prognostic methods can also be utilized to monitor an individual's health status prior to and after therapy, as well as in the assessment of the severity of disease and the likelihood and extent of recovery.

In general, such diagnostic and prognostic methods involve detecting the level of expression or activity of one or more proteins of the GRAIL complex in the cells or tissue of an individual or a sample therefrom. For example, functional assays may detect the number of cells in G0, vs cycling cells. A variety of different assays can be utilized to detect gene expression, including both methods that detect gene transcript and protein levels. The post-translational regulation of GRAIL makes protein detection of particular interest. More specifically, the diagnostic and prognostic methods disclosed herein involve obtaining a sample from an individual and determining at least qualitatively, and preferably quantitatively, the level of the specific polynucleotide or protein of interest in the sample. Usually this determined value or test value is compared against some type of reference or baseline value.

Nucleic acids or binding members such as antibodies that are specific for GRAIL complex proteins are used to screen patient samples for increased expression of the corresponding mRNA or protein, or for the presence of amplified DNA in the cell. Samples can be obtained from a variety of sources. For example, since the methods are designed primarily to diagnosis and assess risk factors for humans, samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from whole blood, serum, semen, saliva, tears, urine, fecal material, sweat, buccal, skin, spinal fluid and amniotic fluid. Also included in the term are derivatives and fractions of such cells and fluids. Samples can also be derived from in vitro cell cultures, including the growth medium, recombinant cells and cell components. The number of cells in a sample will often be at least about $10^2$, usually at least $10^3$, and may be about $10^4$ or more. The cells may be dissociated, in the case of solid tissues, or tissue sections may be analyzed. Alternatively a lysate of the cells may be prepared.

Diagnostic samples are collected any time after an individual is suspected to have had an autoimmune episode, presence of tumor, and the like. In prophylactic testing, samples can be obtained from an individual who present with risk factors that indicate a susceptibility to autoimmune disease or cancer as part of a routine assessment of the individual's health status.

The various test values determined for a sample typically are compared against a baseline value to assess the extent of altered expression, if any. This baseline value can be any of a number of different values. In some instances, the baseline value is a value established in a trial using a healthy cell or tissue sample that is run in parallel with the test sample. Alternatively, the baseline value can be a statistical value (e.g., a mean or average) established from a population of control cells or individuals. For example, the baseline value can be a value or range that is characteristic of a control individual or control population. For instance, the baseline value can be a statistical value or range that is reflective of expression levels for the general population, or more specifically, healthy individuals.

Nucleic Acid Screening Methods

Some of the diagnostic and prognostic methods that involve the detection of GRAIL complex transcripts begin with the lysis of cells and subsequent purification of nucleic acids from other cellular material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include, but are not limited to, mRNA transcripts, cDNA reverse transcribed from the mRNA, cRNA transcribed from the cDNA, DNA amplified from GRAIL complex nucleic acids, and RNA transcribed from amplified DNA.

A number of methods are available for analyzing nucleic acids for the presence of a specific sequence, e.g. altered expression. The nucleic acid may be amplified by conventional techniques, such as the polymerase chain reaction (PCR), to provide sufficient amounts for analysis. The use of the polymerase chain reaction is described in Saiki et al. (1985) Science 239:487, and a review of techniques may be found in Sambrook, et al. Molecular Cloning: A Laboratory Manual, CSH Press 1989, pp. 14.2-14.33.

A detectable label may be included in an amplification reaction. Suitable labels include fluorochromes, e.g. fluorescein isothiocyanate (FITC), rhodamine, Texas Red, phycoerythrin, allophycocyanin,6-carboxyfluorescein(6-FAM),2, 7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes is then contacted with the cells and the probes allowed to hybridize with the nucleic acids of interest. Excess probe is digested, washed away and the amount of hybridized probe measured. This approach is described in greater detail by Harris, D. W. (1996) Anal. Biochem. 243: 249-256; Singer, et al. (1986) Biotechniques 4:230-250; Haase et al. (1984) Methods in Virology, vol. V11, pp. 189-226; and Nucleic Acid Hybridization: A Practical Approach (Hames, et al., eds., 1987).

A variety of so-called "real time amplification" methods or "real time quantitative PCR" methods can also be utilized to determine the quantity of specific mRNA present in a sample. Such methods involve measuring the amount of amplification product formed during an amplification process. Fluorogenic nuclease assays are one specific example of a real time quantitation method that can be used to detect and quantitate transcripts of interest. In general such assays continuously measure PCR product accumulation using a dual-labeled fluorogenic oligonucleotide probe—an approach frequently referred to in the literature simply as the "TaqMan" method.

The probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For measuring a transcript, the probe is designed to have at least substantial sequence complementarity with a probe binding site on an GRAIL complex gene. Upstream and downstream PCR primers that bind to regions that flank the GRAIL complex gene are also added to the reaction mixture. Probes may also be made by in vitro transcription methods.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter dye from the polynucleotide-quencher complex and resulting in an increase of reporter emission intensity that can be measured by an appropriate detection system.

One detector that is specifically adapted for measuring fluorescence emissions such as those created during a fluorogenic assay is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Additional details regarding the theory and operation of fluorogenic methods for making real time determinations of the concentration of amplification products are described, for example, in U.S. Pat. Nos. 5,210,015 to Gelfand, 5,538,848 to Livak, et al., and 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety.

Polypeptide Screening Methods

Screening for expression GRAIL complex may be based on the functional or antigenic characteristics of the protein. Protein truncation assays are useful in detecting deletions that may affect the biological activity of the protein. The activity of the encoded protein may be determined by comparison with the wild-type protein.

Detection may utilize staining of cells or histological sections, performed in accordance with conventional methods, using antibodies or other specific binding members that specifically bind to the protein of interest. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and the polypeptide of interest in a lysate. Measuring the concentration of the target protein in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of the test protein is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7-8, is used as a wash medium.

From one to six washes may be employed, with sufficient volume to thoroughly wash non-specifically bound proteins present in the sample.

After washing, a solution containing a second antibody is applied. The antibody will bind to one of the proteins of interest with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemilumninescers, colloidal particles, and the like. Examples of labels that permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hours is sufficient, usually 1 hour sufficing.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the polypeptide as desired, conveniently using a labeling method as described for the sandwich assay.

In some cases, a competitive assay will be used. In addition to the patient sample, a competitor to the targeted protein is added to the reaction mix. The competitor and the GRAIL complex compete for binding to the specific binding partner. Usually, the competitor molecule will be labeled and detected as previously described, where the amount of competitor binding will be proportional to the amount of target protein present. The concentration of competitor molecule will be from about 10 times the maximum anticipated protein concentration to about equal concentration in order to make the most sensitive and linear range of detection.

In some embodiments, the methods are adapted for use in vivo, e.g., to locate or identify the state of T cells in a tissue. For example, the tolerance/anergic state of T cells in an autoimmune lesion, graft, etc. may be determined. In these embodiments, a detectably-labeled moiety, e.g., an antibody, which is specific for a polypeptide of the GRAIL complex is administered to an individual (e.g., by injection), and labeled cells are located using standard imaging techniques, including, but not limited to, magnetic resonance imaging, computed tomography scanning, and the like.

Activities of polypeptides of the GRAIL complex can also be determined to detect an alteration in expression. Certain assays involve detecting an increase or decrease in steady state protein levels in a sample from a patient, relative to a baseline value. Assays can be conducted using isolated cells or tissue-samples:

The detection methods can be provided as part of a kit. Procedures using these kits can be performed by clinical laboratories, experimental laboratories, medical practitioners, or private individuals. The kits of the invention for detecting a polypeptide comprise a moiety that specifically binds the polypeptide, which may be a specific antibody. The kits of the invention for detecting a nucleic acid comprise a moiety that specifically hybridizes to such a nucleic acid. The kit may optionally provide additional components that are useful in the procedure, including, but not limited to, buffers, developing reagents, labels, reacting surfaces, means for detection, control samples, standards, instructions, and interpretive information.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Studies described below characterize two proteins, DOG and SOG, each a separate splice variant of the same gene, OTUBAIN-1, that interact to stabilize or destabilize GRAIL and thus the outcome of anergy induction.

GRAIL forms a complex with otubain-1. A yeast two-hybrid system was used to identify GRAIL binding partners. Since GRAIL is constitutively expressed in the liver, we used a cDNA library from mouse liver, fused to the myristolation signal of the pMyr plasmid. The C-terminus of GRAIL, downstream of the transmembrane domain, was used as bait, fused to hSOS. From more than 500,000 clones analyzed, five positive clones were found to specifically interact with the C-terminus of GRAIL. These are listed in Table I as clones 5C-27 through 6C-12, with their closest sequence homologue.

TABLE I

| CLONE | SEQUENCE HOMOLOGY |
|---|---|
| 5C-27 | 98% identical to human E2-H5a |
| 5C-28 | 97% identical to FLJ11673 (similar to E2-18 kDa) |
| 6C-17 | 98% identical to FLJ13988 (similar to E2-18 kDa) |
| 6A-36 | 98% identical to human FLJ20113 (OTUBAIN-1) |
| 6C-12 | 100% identical to human E2-H5c |

Table I: A mouse liver library cloned into pMyr vector was purchased from Stratagene (La Jolla, CA). The C-terminal half of GRAIL, starting at F225 was PCR amplified, cloned into the pSOS vector, and used as bait. Yeast competent cells were co-transformed with either the bait and library or control vectors as described in the CytoTrap instruction manual (Stratagene). More than 5 x 10$^5$ clones were screened. Colonies displaying growth on galactose but not glucose at 37° C. were considered to be putative positives and were evaluated in a secondary screen. Colonies growing in the secondary screen on galactose at 37° C. and in the presence of the GRAIL-SOS bait vector, but not the SOS vector alone, were considered true interactors and sequenced.

GRAIL is an E3 ligase, and three of the cDNAs pulled down in the yeast-two hybrid assay encoded E2 conjugating enzymes, including a novel E2 with limited homology to the E2-18 kD-like E2-ubiquitin conjugating enzyme. One clone had a 525 bp insert with very high homology to a hypothetical human protein containing a predicted ovarian tumor domain (OTU) (Makarova et al. (2000) *Trends Biochem Sci*, 25, 50-52). Searching PFAM for proteins with similar domain structures, three *C. elegans* ubiquitin carboxy-terminal hydrolases (F38B7.5, F29C4.5 and Y106G6H. 12) were discovered that contained an OTU domain inserted between two halves of the Ubiquitin Carboxy-Hydrolase (UCH) domain. A *drosophila* protein homologue with no known function was also identified, CG4603, that contains both a central OTU domain and a N-terminal ubiquitin-like domain. The appearance of the OTU domain in association with domains involved in the ubiquitin pathway suggested that this new GRAIL-interacting protein might play a role in GRAIL biology, thus it was investigated further.

The 525 bp cDNA fragment sequence was blasted against the NCBI human genome database and a single 100% match was obtained for a genome scan predicted ORF on chromosome 11. The prediction was also supported by mRNA data from the NEDO human cDNA sequencing project (accession #NM_017670) in which it was classified as *Homo sapiens* hypothetical protein FLJ20113. Recently this gene was identified as OTUBAIN-1, a member of a new class of ubiquitin specific protease with specificity toward isolated branched polyubiquitin chains (Balakirev et al. (2003) *EMBO Rep*, 4, 517-522). Oligonucleotide primers for the predicted coding sequence identified OTUBAIN-1 mRNA expression in several human tissues by PCR. Agarose gel analysis of the mRNA PCR reaction revealed the presence of a second fragment of about 950 bp (FIG. 1.A), seen preferentially expressed in secondary lymphoid tissues (FIG. 1B). By Immunoblot analysis, using a rabbit anti-OTUBAIN-1 antibody, several additional isoforms were identified (FIG. 1C). Both OTUBAIN-1 PCR products were cloned and sequenced. Sequencing the smaller 815 bp product produced a sequence with 100% homology to the OTUBAIN-1 coding sequence. The sequence of the larger PCR product represented an alternative spliced mRNA that had an additional 210 bp of coding sequence in the central region of the mRNA.

Both sequenced products were in vitro translated with $S^{35}$ Methionine and the labeled proteins were subjected to a pull-down assay with a bacterial recombinant GST-GRAIL fusion protein (FIG. 2A). Both cDNAs were also subcloned into the pc*DNA3.1 mammalian expression vector with their 3' ends fused in frame with an HSV epitope-Tag. The plasmids were co-transfected with GRAIL into 293 human embryonic kidney cells, and cell lysates were analyzed for expression of the HSV labeled products, and for GRAIL association by immunoprecipitation and immunoblot analysis (FIG. 2B). The shorter isoform cDNA gave rise to a 31 KDa protein and the larger isoform to a 35 KDa protein. Both isoforms co-precipitated with GRAIL in the pull-down assays as well as in the immunoprecipitation assays. An intact GRAIL RING domain was not required for the association. For analysis of this association in a more physiological setting we prepared whole liver extracts and precipitated OTUBAIN-1 and GRAIL with specific polyclonal antibodies. Immunoblot of the immunoprecipitates with an anti-GRAIL monoclonal antibody revealed that OTUBAIN-1 and GRAIL associate with one another in the liver. (FIG. 2C)

Analysis of the coding sequence of the larger isoform using the DNA translation and mass prediction tools at ExPASy, revealed that an alternative reading frame must be used in order to produce the observed protein with a mass of 35 Kda that incorporates a different AUG codon in exon 2. This is achieved by using a read-through mechanism where there is no splicing between exons 4 and 5 (using the genome scan scheme) causing a frame-shift at the 5' end of exon 5, thus changing the reading back to frame+1 (FIG. 3A). The result is that both isoforms of OTUBAIN-1 have identical c-terminal 140 amino acids, including the GRAIL binding domain (FIG. 3B). As a consequence of this arrangement, the larger 35 kDa isoform (initially called OTUBAIN-1 ARF-1, for alternative reading frame 1) lacks two of the three amino acids (Asp and Cys) that compose the signature OTU cysteine proteinase catalytic core of the original OTUBAIN-1, and retains only the C-terminal flanking region of the OTU domain.

A human tissue mRNA panel was tested by northern analysis for the presence of transcripts of both isoforms. The shorter isoform was found to be expressed ubiquitously, whereas the longer isoform had a somewhat restricted expression pattern; detectable in the tonsil, lymph node, peripheral blood mononuclear cells (PBMC) and spleen (FIG. 1B). Interestingly, northern blot analysis of OTUBAIN-1 expression in tissues of the human immune system revealed the presence of at least four distinct transcripts hybridizing to the OTUBAIN-1 probe. An inquiry at the NCBI AceView for this locus on human chromosome 11 (HSPC263) provided supporting evidence for the presence of multiple different transcripts encoding at least 13 different protein isoforms. Only one of the multiple transcripts encoded the full OTU domain-containing protein (sukera transcript a), the 31 kDa isoform encoding OTUBAIN-1. Another transcript (sukera c) encoded the 35 kDa isoform, OTUBAIN-1 ARF-1. Immunoblot analysis of human PBMC with OTUBAIN-1 specific antiserum revealed the presence of two major bands, a 31 kDa isoform (OTUBAIN-1) and a 40 kDa isoform (likely transcript h, a transcript that is identical to the isoform encoding OTUBAIN-1 ARF-1, except for an in-frame 36 amino acid insertion downstream from exon 5), while a blot of the murine ANTC T cell hybridoma lysate demonstrated the presence of 31 kDa, 35 kDa, and 40 kDa isoforms as well as a larger band of about 52 kDa (likely transcript g) (FIG. 1C). These results indicate that OTUBAIN-1 is capable of generating multiple transcripts.

Figure 4:
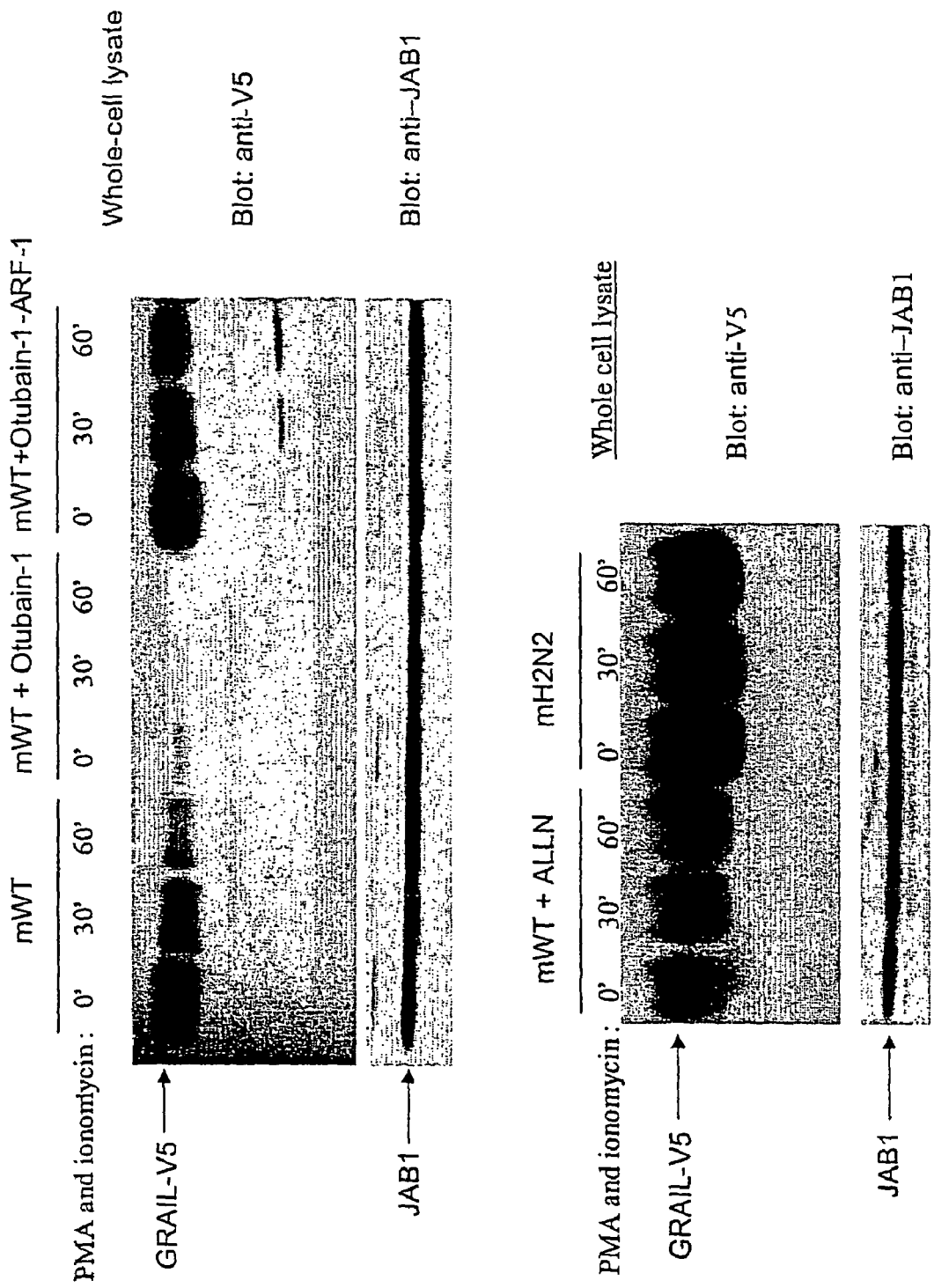
FIG. 4. Stimulation-dependent degradation of GRAIL is enhanced by DOG and inhibited by SOG. A) ANTC mouse T cell hybridomas stably expressing GRAIL, H2N2-GRAIL, or a combination of GRAIL and DOG or GRAIL and SOG, were stimulated for the indicated times with PMA/ionomycin. Whole cell lysates were prepared and analyzed by immunoblot after SDS-PAGE. For the ALLN experiment, ANTC cells were incubated at 37° C. for 1 hour with 25 μM ALLN prior to the addition of PMA/ionomycin. Immunoblot against JAB-1 served as a loading control. The results shown represent one of six independent experiments. Five independent cell lines double-expressing DOG/SOG and GRAIL were tested with similar results. B) 293 cells were co-transfected with equivalent (1 µg/well) concentrations of the indicated plasmid pairs. 48 hours later whole cell lysates were separated by SDS-PAGE and analyzed by immunoblot with anti-V5 antibody. C). $1\times10^6$ ANTC mouse T cell hybridomas, stably expressing GRAIL, DOG, SOG, or combinations of GRAIL and DOG or SOG, were stimulated in triplicate for 8 hours with PMA/ionomycin. Supernatants were collected and analyzed for IL-2 content by ELISA and the data are expressed as arbitrary units of IL-2/ml.

OTUBAIN-1 and OTUBAIN-1 ARF-1 are epistatic regulators of GRAIL with opposing functions. To test whether the 31 and 35 kDA isoforms of OTUBAIN-1 could influence GRAIL function in T cells, both isoforms were subcloned into the pEF6 vector and transferred into GRAIL-GFP positive murine T cell hybridomas. Positive transfectants were selected by limiting dilution based on blasticidin resistance and GFP expression. In T cells, GRAIL is relatively short lived after stimulation with TCR agonists, such as PMA and ionomycin or a combination of anti-CD3 and anti-CD28 (FIG. 4A). GRAIL mutants that lack an intact RING domain are much more stable, and the stability of WT GRAIL is significantly enhanced by the proteasome inhibitor ALLN, implicating auto-ubiquitination in GRAIL degradation. Co-expression of OTUBAIN-1 with GRAIL caused GRAIL to completely disappear from the hybridomas. Expression of the OTUBAIN-1-ARF-1 isoform in GRAIL expressing hybridomas had the opposite effect; it caused an increase in baseline levels of GRAIL and prevented its activation-induced degradation. No changes in GRAIL mRNA levels were observed.

Figure 4B:
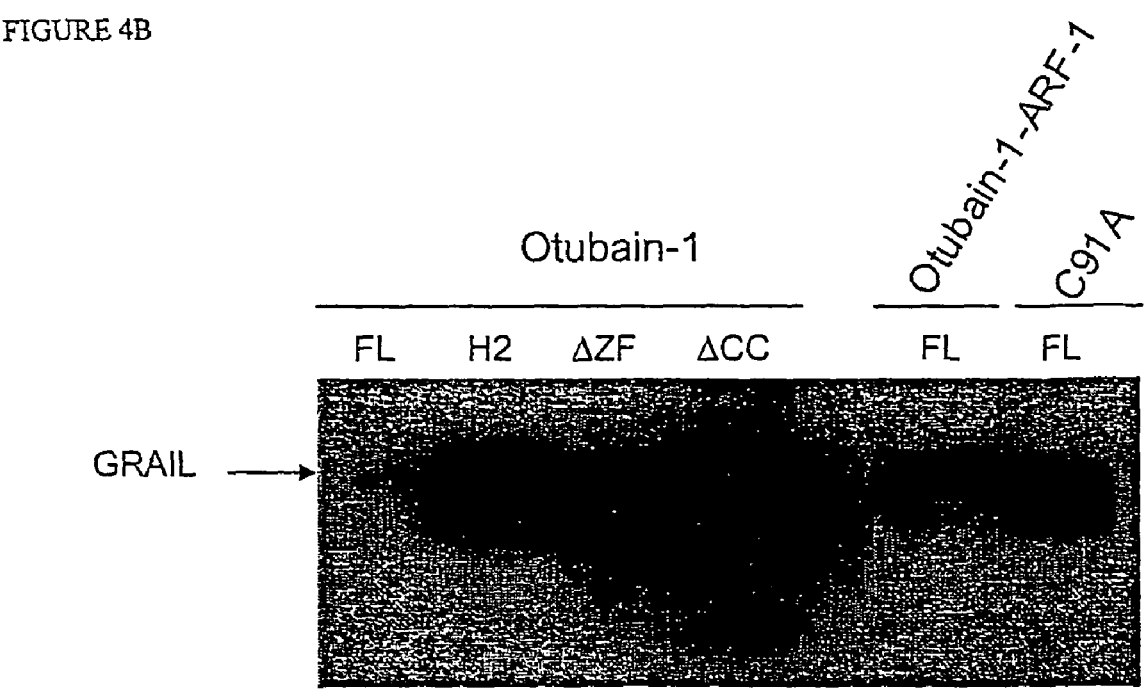
Figure 4:
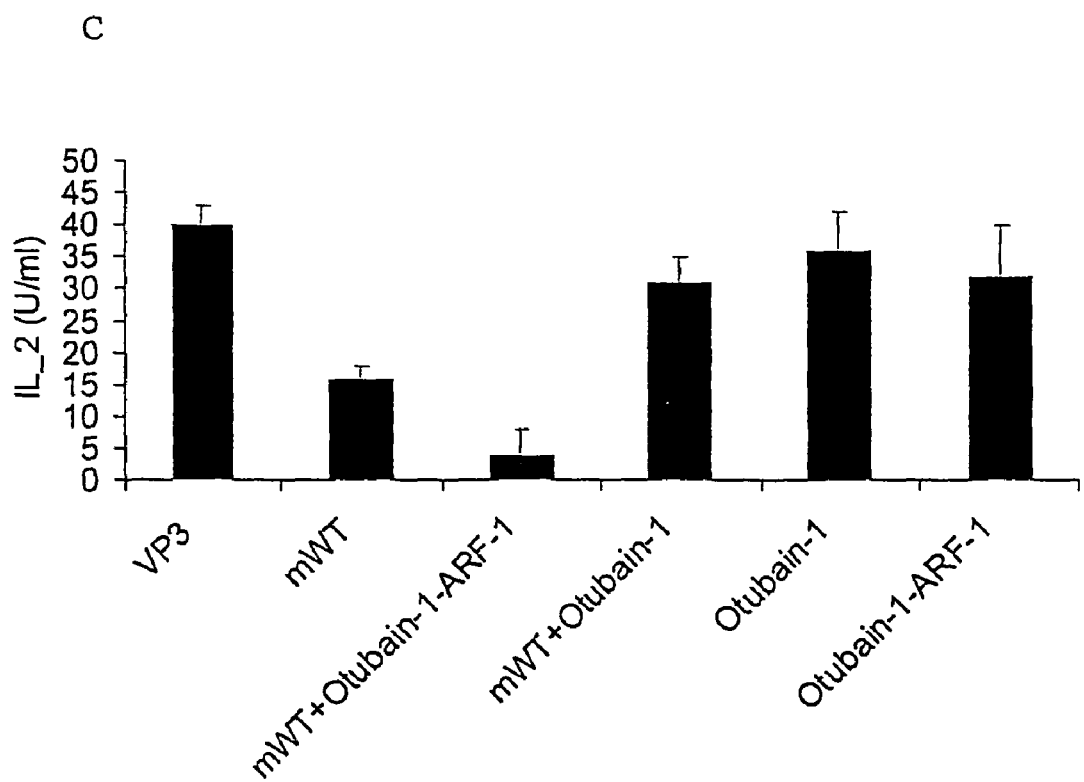

In 293 cells, co-expression of OTUBAIN-1 with wild type GRAIL caused GRAIL levels to drop dramatically. Co-expression of GRAIL and OTUBAIN-1 ARF-1 in 293 cells stabilized GRAIL expression to approximately the same extent as did a catalytic domain mutant of OTUBAIN-1 where the cysteine at position 91 was replaced with an arginine (C91A) (FIG. 4B). We also tested murine T cell hybridomas co-expressing GRAIL and OTUBAIN-1 or GRAIL and OTUBAIN-1 ARF-1 for IL-2 production after PMA and ionomycin stimulation, and found that OTUBAIN-1 ARF-1 increased the inhibitory effect of GRAIL on IL-2 production, while OTUBAIN-1 had the opposite effect (FIG. 4C). In the absence of endogenous GRAIL expression, neither OTU-BAIN-1 or OTUBAIN-1 ARF-1 affected IL-2 production in the T cell hybridomas. Because of these opposing regulatory roles on GRAIL stability (and expression), we renamed the two isoforms DOG, for Destabilizer of GRAIL (previously OTUBAIN-1) and SOG for Stabilizer of GRAIL (previously OTUBAIN-1 ARF-1).

Figure 5:
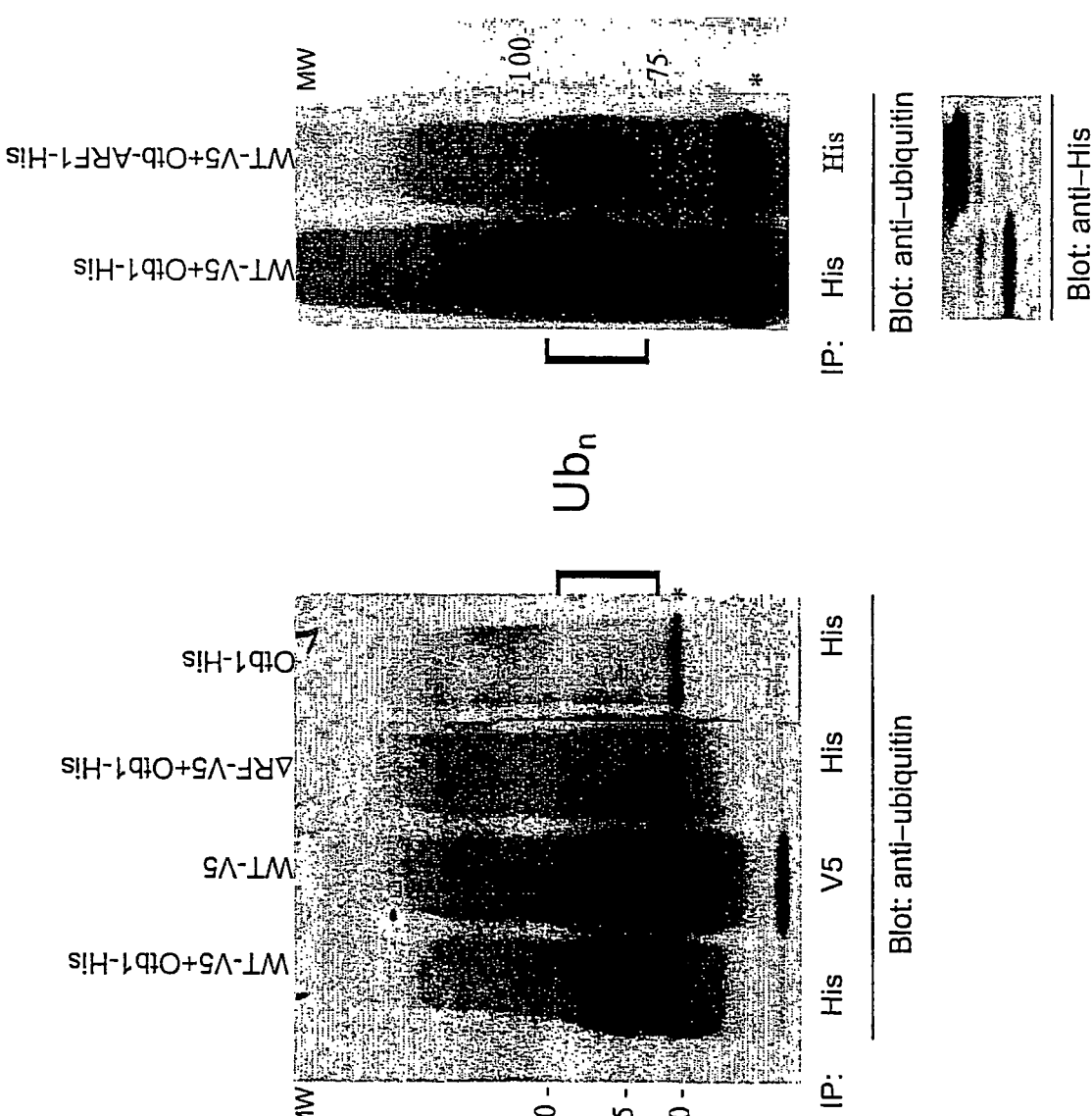
FIG. 5. DOG regulates GRAIL-mediated ubiquitination. A) 293 cells were transfected with the indicated constructs at a ratio of 3 parts of GRAIL to 1 part of all other partners (3:1 ratio)(WT=wild type GRAIL-V5; ΔRF=a ring finger deletion of GRAIL). 48 hours post-transfection, cell lysates were prepared (2 mg) and immunoprecipitated (i.p) with the indicated antibodies. Immunocomplexes were resolved by SDS-PAGE, transferred to a PVDF membrane, and immunoblotted with anti-ubiquitin antibody. B) 293 cells were co-transfected with GRAIL-V5 and Flag tagged ubiquitin constructs alone or in combination with a DOG construct (3:1 ratio). Cell lysates were prepared and divided into two parts. One part (1 mg) (non-denaturing) was immunoprecipitated with anti-V5 antibody. SDS was added to the other part (1 mg) (denaturing) to a final concentration of 1% and the samples were incubated for an additional 30 minutes. Prior to immunoprecipitation with anti-V5 antibody, samples were diluted with SDS-free lysis buffer so that the final concentration of SDS was less than 0.1%. Immunocomplexes were resolved by SDS-PAGE, transferred to PVDF and immunoblotted with anti-Flag antibody to reveal ubiquitination. C) 293 cells were co-transfected with GRAIL-V5 and Flag tagged ubiquitin constructs alone or in combination with several DOG constructs (3:1 ratio). DOG-C91A represents a catalytically inactive OTU domain (cysteine to alanine at position 91 of human DOG); C212A and R176L represent mutations in other conserved residues in the OTU domain. 48 hours post transfection, cell lysates (2 mg) were immunoprecipitated with anti-V5 antibody. Immunocomplexes were resolved by SDS-PAGE, transferred to PVDF and immunoblotted with anti-Flag antibody to reveal ubiquitination. D) 293 cells were transfected as in "C" and cell lysates were immunoblotted for Flag to reveal total cellular ubiquitination. E) 293 cells were transfected with the indicated constructs and lysates (5 mg) immunoprecipitated with anti-Flag antibody. Immunocomplexes were resolved by SDS-PAGE, transferred to PVDF and immunoblotted with anti-V5 antibody.
Figure 5:
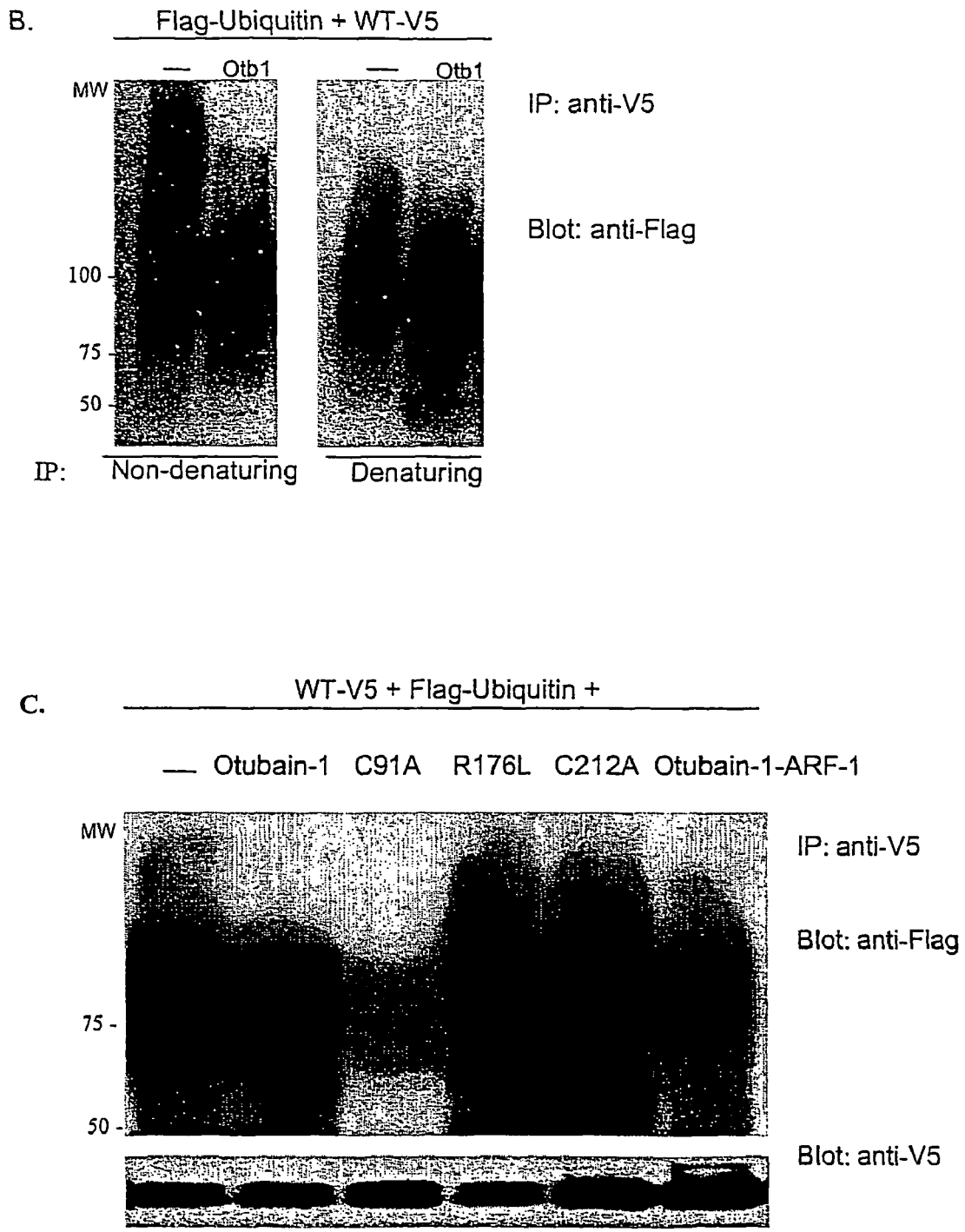
Figure 5:
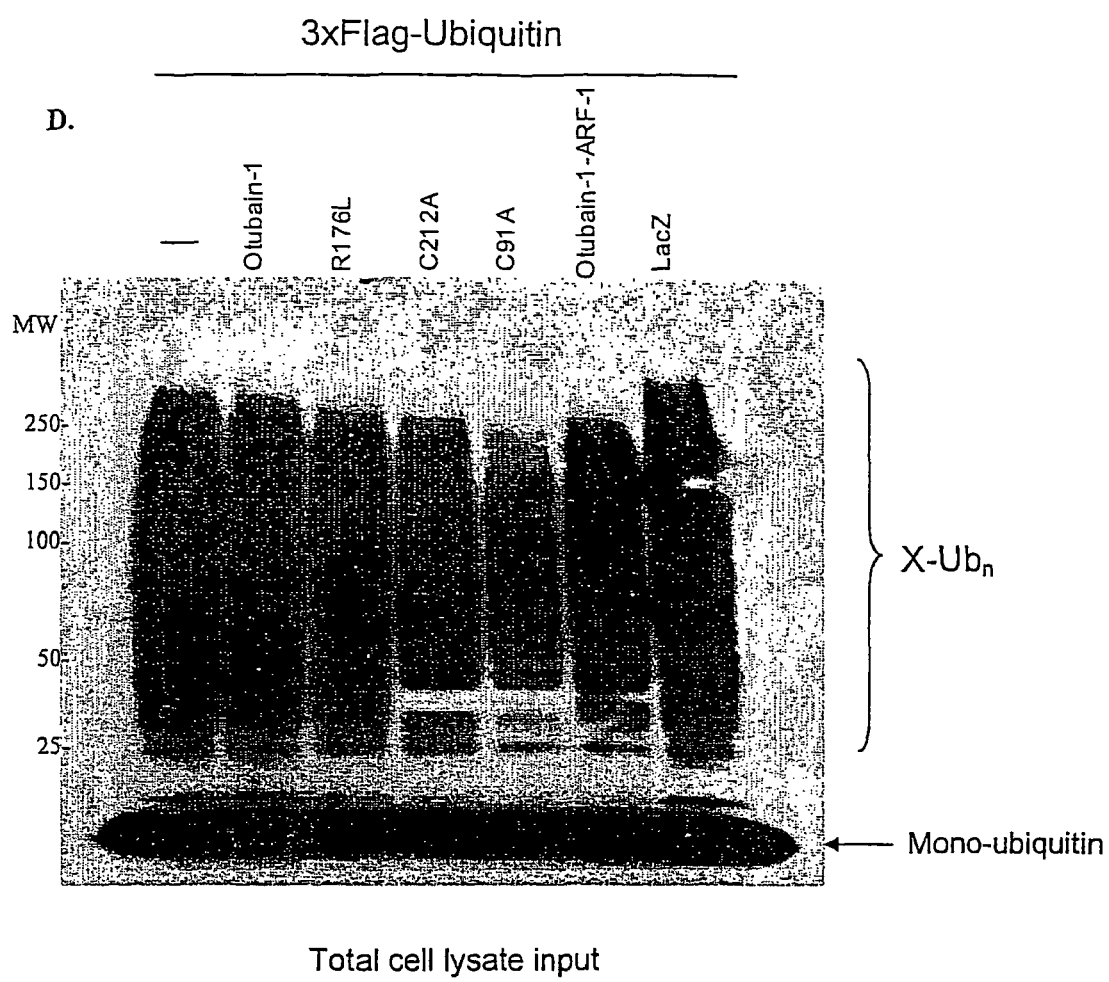

DOG regulates GRAIL-mediated ubiquitination. Since co-expression of DOG with GRAIL caused GRAIL instability, and since GRAIL lacking a RING domain was stable in the presence of DOG and because GRAIL stability was enhanced by proteasome inhibitors, we considered the possibility that DOG (OTUBAIN-1) may in some manner influence the level of GRAIL auto-ubiquitination. To test this hypothesis we transfected 293 cells with wild type GRAIL, or with a mutant lacking the RING domain, along with DOG or SOG (OTUBAIN-1 ARF-1), and looked for associated ubiquitinated targets by immunoblot following immunoprecipitation. As shown by data presented in FIG. 5A, a substantial fraction of the GRAIL-dependent ubiquitinated proteins could be recovered in DOG immunoprecipitates in cells co-expressing GRAIL and DOG. GRAIL dependent protein ubiquitination required an intact RING domain and was significantly reduced in SOG immunoprecipitates from cells transfected to express GRAIL and SOG. The ubiquitination pattern observed in the GRAIL immunoprecipitates was largely retained after treatment of the lysate with 1% SDS, indicating auto-ubiquitination (FIG. 5B).

Because a fundamental difference between DOG and SOG is the absence of the catalytic domain in SOG, we produced a catalytic mutant of DOG by substituting the active cysteine (FIG. 3) with an alanine residue (DOG C91A). Also, in order to improve the definition in the blots, we made use of a Flag-tagged ubiquitin construct. Surprisingly, GRAIL immunoprecipitates of lysates of cells co-expressing DOG C91A produced virtually no ubiquitinated protein signal, while cells co-expressing SOG and GRAIL produced a small amount of signal (FIG. 5C). Interestingly, additional immunoprecipitation studies using a larger amount of lysate (5 mg, compared to 2 mg) produced a clear pattern of mono or di-ubiquination of proteins in cells co-expressing either SOG, or the catalytically inactive DOG C91A along with GRAIL (FIG. 5E). Thus, an intact OTU-like catalytic domain in DOG was an absolute requirement for GRAIL-mediated protein ubiquitination. Because DOG is constitutively expressed in the cells being studied, the catalytically inactive form of DOG, DOG C91A, may be functioning as a dominant negative enzyme in this setting.

As shown by data presented in FIG. 6, DOG has potent DUB activity toward free branched K48-linked polyubiquitin chains. The results of experiments where DOG and GRAIL are co-expressed in cells, do not give any indication that DOG works as a DUB toward ubiquitinated GRAIL (see FIG. 6). Recombinant *E. Coli* DOG also had no DUB activity in vitro toward ubiquitinated GRAIL as demonstrated by data presented in FIG. 6D. In addition, if DOG had DUB activity toward GRAIL, the catalytically inactive DOG C91A mutant should increase GRAIL-mediated auto-ubiquitination. However, GRAIL auto-ubiquitination in the presence of DOG C91A was decreased compared to GRAIL auto-ubiquitination in the presence of DOG. (FIG. 5C-E). Because DOG disassembles free branched polyubiquitin chains in vitro, it might be expected to function in ubiquitin recycling, just as the proteosome-associated DUB, UCH37 does. If this were true, the C91A mutant of DOG should effectively block ubiquitin recycling, leading to exhaustion of the pool of free ubiquitin and prevention of new ubiquitination via E3 ligases. However, the pool of free ubiquitin, as detected by immunoblot, was unchanged in cells expressing DOG C91A, when compared to cells expressing wild-type DOG (FIG. 5D). We also considered the possibility that DOG might function as a specific receptor associated with the proteasome, for ubiquitinated GRAIL, but the observation that GRAIL basal levels were substantially increased in cells co-expressing DOG C91A, demonstrating that the accumulated GRAIL was not ubiquitinated, argued against this possibility. To our knowledge this is the first demonstration of a role for any OTU domain containing protein in the regulation of RING E3-dependent ubiquitination.

DOG forms a tri-molecular complex with GRAIL and the ubiquitin-specific protease UBPy/USP8 DOG can be rescued on an affinity column containing thiol-reactive ubiquitin-like probes, such as ubiquitin aldehyde or other derivatives. Since DOG binds ubiquitin non-covalently, we employed a bacterial two-hybrid screen using DOG as bait (in order to avoid the background binding from endogenous ubiquitin that was encountered in the yeast two-hybrid assay for DOG). Using the bacterial two-hybrid system, we screened a mouse liver cDNA library and rescued a cDNA fragment that corresponded to the catalytic domain of the DUB enzyme UBPy, also known as USP8. Analysis of UBPy/USP8 in PFAM identified two recognizable domains, a c-terminal UCH catalytic domain, and an n-terminal rhodanese domain of unknown function.

Figure 7:
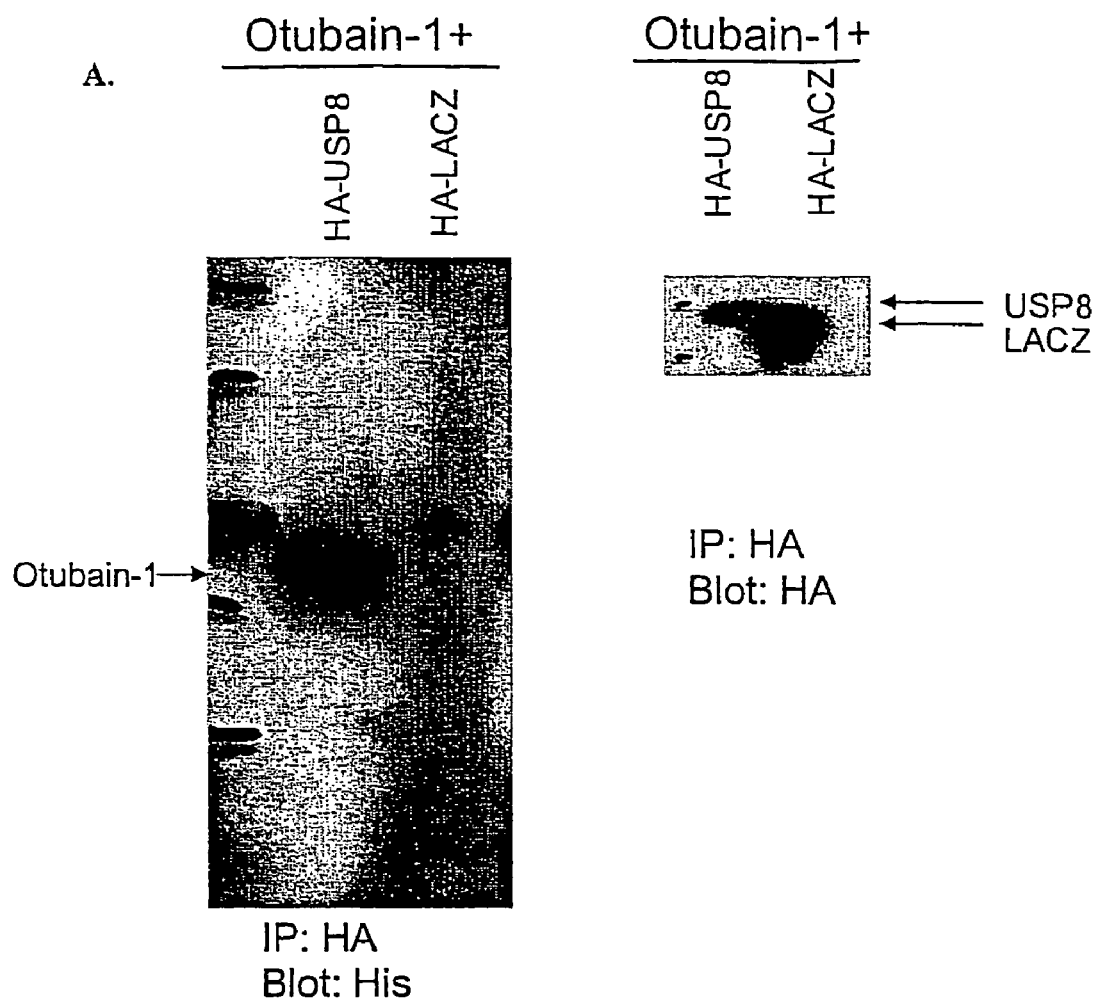
FIG. 7. GRAIL, DOG and USP8 form a tri-molecular complex in cells. A) 293 cells were co-transfected with HA-tagged USP8 and DOG-His plasmids, or HA-tagged LacZ as a control. 48 hours after transfection cell lysates were prepared and immunoprecipitated with anti-HA antibody. Immunocomplexes were resolved by SDS-PAGE, transferred to PVDF and immunoblotted with either anti-His or anti-HA antibodies. B) 293 cells were co-transfected with HA-USP8, GRAIL-V5 and/or a c-terminal truncation of USP8 (HA-USP8 ΔC).) and a catalytically inactive form of USP8 (C748A) (3:1 ratio). 48 hours after transfection cell lysates were prepared and immunoprecipitated with anti-HA antibody. Samples were treated as in "A" and immunoblotted sequentially with anti-V5 (GRAIL), anti-His(DOG) and anti-HA (USP8) antibodies. (C) E. coli BL21 bacteria were co-transformed with the bacterial bicistronic plasmid pACYC Duet (Novagen) carrying a copy of the human UbB gene (containing a His Tag) and either wild-type DOG or DOG-C91A along with a compatible pET28 plasmid containing USP8. Liquid cultures were induced with IPTG for 3 hours at 34° C. and total cell lysates were prepared every 1 hour, resolved by SDS-PAGE, transferred to PVDF and immunoblotted with anti-His antibody to reveal cleavage of the ubiquitin precursor. (D) DOG-HSV or SOG-HSV tagged was co-transfected with HA-USP8 in 293 cells. 48 hours after transfection cell lysates were prepared and immunoprecipitated with anti-HA antibody. Immunocomplexes were resolved by SDS-PAGE, transferred to PVDF and immunoblotted with either anti-HSV or anti-HA antibodies. E) 293 cells were co-transfected with GRAIL-V5, HA-USP8-C748A, with or without SOG-HSV. 48 hours after transfection cell lysates were prepared and immunoprecipitated with anti-HA antibody. Immunocomplexes were resolved by SDS-PAGE, transferred to PVDF and immunoblotted with anti-V5 antibody. F) 293 cells were transfected with increasing amounts of SOG-HSV and a fixed amount of GRAIL-V5 (2 ug) and DOG-His (1 ug). Total DNA transfected was kept constant by inclusion of pUC18 as a carrier. 48 hours after transfection cell lysates were prepared and immunoprecipitated with anti-V5 antibody. Immunocomplexes were resolved by SDS-PAGE, transferred to PVDF and immunoblotted with either anti-HSV or anti-His antibodies.
Figure 7:
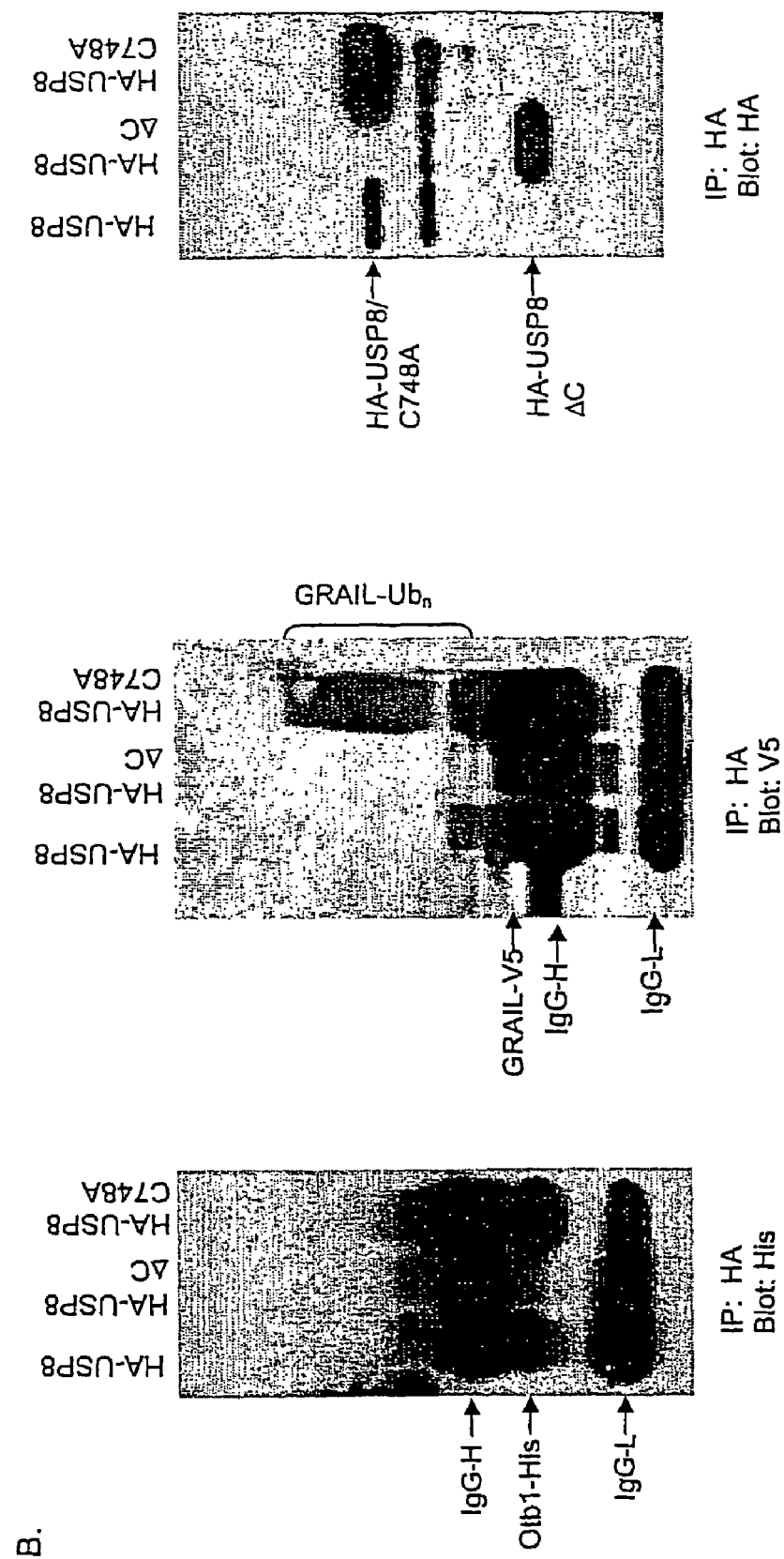
Figure 7:
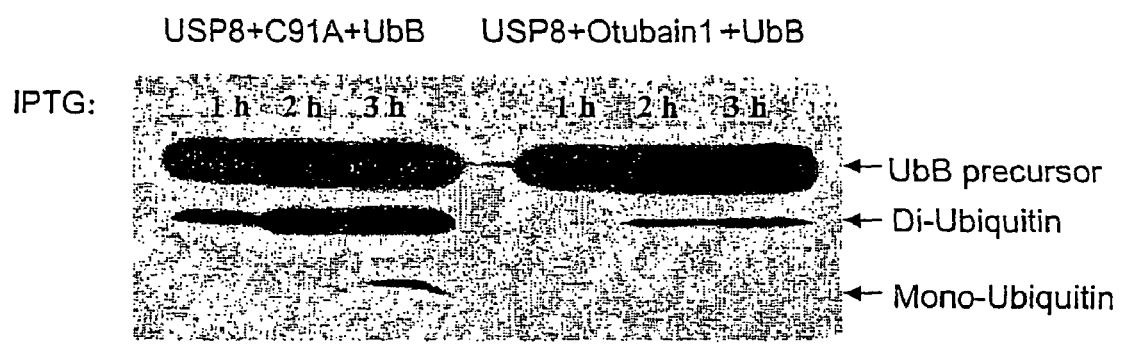
Figure 7:
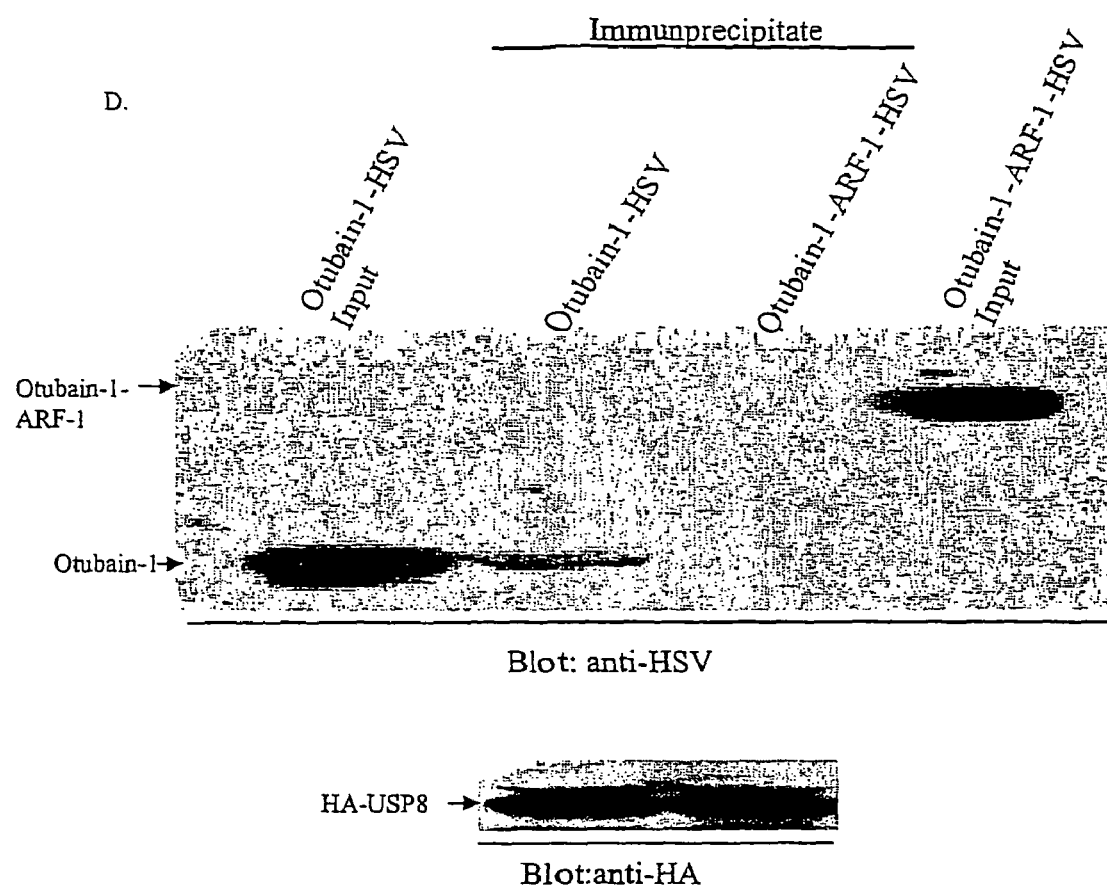
Figure 7:
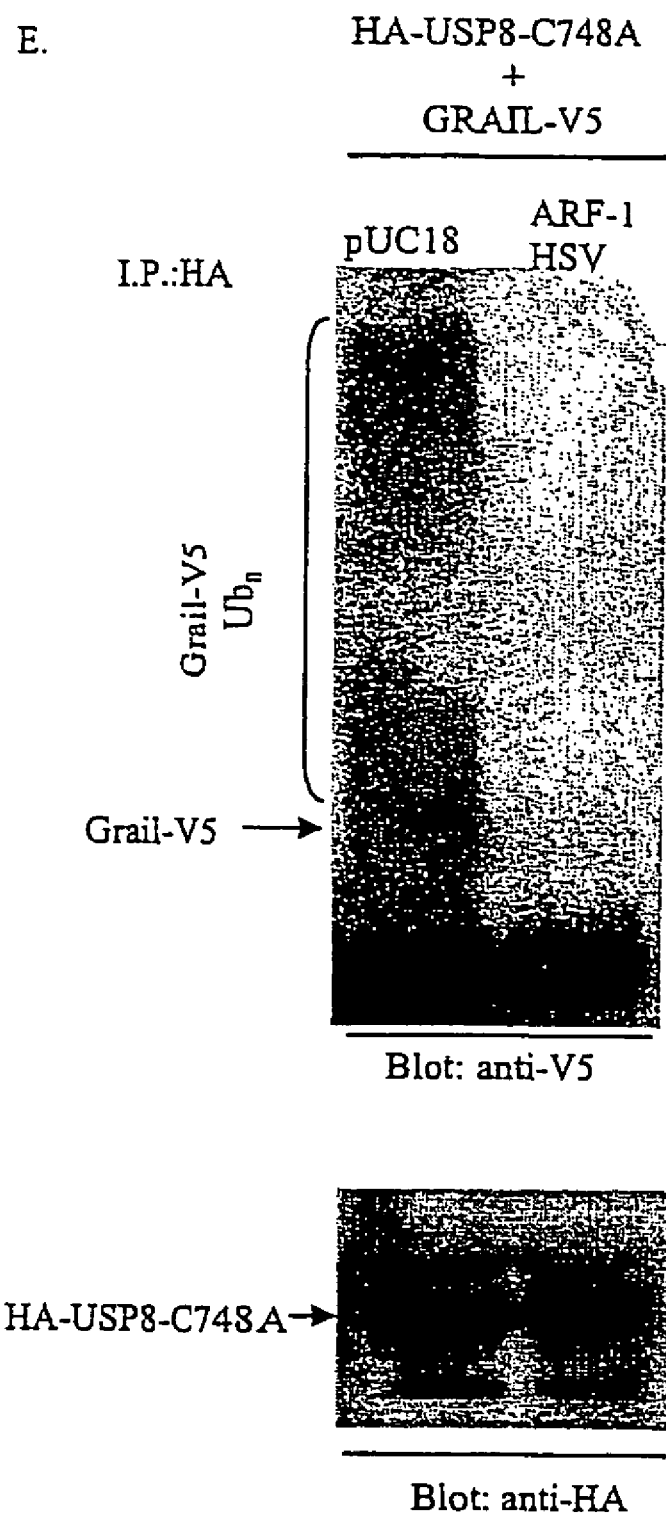
Figure 7:
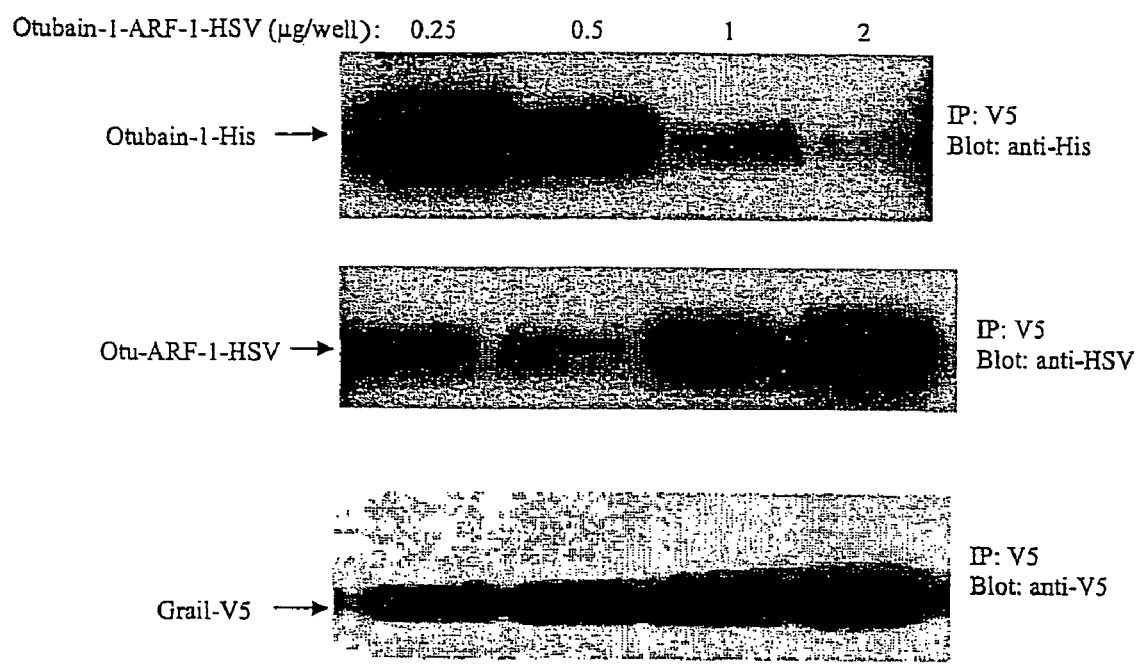

Expression of DOG and different USP8 constructs in 293 cells demonstrated that DOG bound to USP8 specifically; no binding was detected to a control protein expressing the same Tag as USAP8 (FIG. 7A). Binding was also specific to the catalytic domain of USP8; binding to a c-terminal truncated USP8 containing only the rhodanese domain was greatly reduced (FIG. 7B). To test whether a DOG-USP8 complex associated with GRAIL, we co-expressed the three cDNAs (DOG, GRAIL, and USP8) in 293 cells. Immunoprecipitates of USP8 also contained DOG and GRAIL (FIG. 7B) indicating that DOG, GRAIL and USP8 exist as a tri-molecular complex in cells. Interestingly, despite very low levels of interaction between USP8ΔC and DOG, the association of this truncation mutant with GRAIL was only slightly reduced in comparison to wild-type USP8 (FIG. 4B, middle panel). This suggested that GRAIL might be able to interact directly with USP8, or through an unknown partner.

Unlike DOG, USP8 is capable of de-ubiquitinating GRAIL in vitro (FIG. 6D). Because USP8 has broad, but rather non-specific activity when over-expressed in cells, we made a catalytically inactive USP8, where the cysteine at position 748 was exchanged for an alanine (C748A), and demonstrated that this catalytically inactive mutant bound to the GRAIL-DOG complex as well as did the wild-type USP8 (FIG. 7B). Surprisingly, co-expression of the mutant USP8, C748A and GRAIL, caused accumulation of polyubiquitinated GRAIL (FIG. 7C), suggesting that the DOG-USP8 complex is involved in the regulation of GRAIL stability through control of the level of auto-ubiquitination. These data suggest that DOG might directly inhibit the DUB activity of USP8.

To test this hypothesis, we made use of the bacterial co-translational system for DUB activity (FIG. 6C). Using the pACYC-Duet (see Materials and Methods) plasmid, which allows the expression of two independent ORFs, we transformed BL21 bacteria with pACYC-UbB-DOG along with the ori (origin of replication)-compatible pET 28 plasmid carrying a copy of USP8. pACYC-UbB-C91A, pACYC-UbB or an empty pET28 plasmid served as controls. As shown by data presented in FIG. 7D, co-expression of DOG and USP8, but not the catalytically inactive C91A mutant of DOG and USP8, substantially inhibited the generation of mono-ubiquitin via USP8's DUB activity. Taken together these results suggest that DOG may increase the rate of GRAIL auto-ubiquitination by limiting the deubiquitinating activity of USP8 on GRAIL.

When USP8 and SOG were co-expressed, no demonstrable association between these proteins could be identified by immunoprecipitation studies (FIG. 7D). Never-the-less, expression of high levels of SOG, along with the catalytically inactive USP8 C748A, substantially inhibited the accumulation of ubiquitinated GRAIL (FIG. 7E), suggesting that SOG may compete with DOG for GRAIL binding (FIG. 7F), effectively preventing a fraction of the DOG protein from binding GRAIL, and allowing free USP8 to deubiquitinate and thus stabilize GRAIL. Since there is an alternative binding mode for USP8 and GRAIL that does not require DOG (see FIG. 4B) it is quite likely that the competitive interaction between DOG and SOG for GRAIL binding controls access of USP8 to GRAIL, thus controlling the level of GRAIL auto-ubiquitination. More SOG leads to more USP8 activity and stability of GRAIL whereas DOG binds GRAIL effectively preventing deubiquitination by USP8 and destabilized GRAIL expression.

DOG over-expression in naïve T cells caused down-regulation of GRAIL expression and increased antigen induced proliferation, whereas SOG over-expression had the opposite effect. To study the effect of constitutive DOG or SOG expression on endogenous GRAIL activity (anergy induction) in primary CD4+ T cells, hematopoietic stem cells from DO11.10 TCR transgenic mice were retrovirally transduced to express either DOG or SOG and transferred into lethally irradiated BALB/c syngeneic mice. The retroviral construct contained GFP downstream of an IRES sequence and the gene of interest. Constitutive expression of the transgene could be tracked using GFP expression as a marker. FACS analysis prior to transfer into lethally irradiated donors demonstrated transduction of long-term multipotent progenitors with DOG and SOG retrovirus and controls (Sca-1+, c-kit+, lin−). Analysis of the CD4+ T cell lineage in reconstituted mice demonstrated normal development in the thymus of both DOG and SOG expressing T cells as compared to GFP control cells. CD4+ lymph node and spleen cells from DOG, SOG and control reconstituted mice were sorted for GFP expression and stimulated in vitro with irradiated splenocytes from normal BALB/c mice and OVA peptide.

Constitutive DOG expression in naïve CD4+ T cells resulted in increased IL-2 production and enhanced proliferation in response to OVA challenge when compared to the response of the vector transduced cells, while expression of SOG resulted in almost no IL-2 production or proliferation, recapitulating the anergy phenotype (FIG. 8.A). Despite the overall low levels of endogenous GRAIL expression, immunoblot analysis of the transduced bone marrow cells showed further down regulation of endogenous GRAIL levels in DOG expressing BM cells and upregulation in SOG expressing BM cells (FIG. 8.B).

GRAIL has been implicated in the induction of anergy in T cells (Anandasabapathy et al. (2003) *Immunity*, 18, 535-547), but little is known about how it contributes to the anergic phenotype. Due to its localization in the endosomes, it might be involved in the ubiquitination of membrane-associated targets that recycle through these organelles and are important for T cell activation. Although GRAIL is constitutively expressed in some tissues including the liver and brain, expression in T cells is regulated. Thus, GRAIL is expressed only in T cells stimulated in the absence of a classical costimulatory signal, i.e., TCR engagement or ionomycin only. In the work described above it is demonstrated that GRAIL is also regulated at the protein level through the actions of DOG and one of its isoforms, SOG. Like other RING E3 ligases, most notably MDM2, GRAIL regulates its own levels through auto-ubiquitination, as demonstrated by the lack of self-ubiquitination of the ring mutant H2N2 and the consequent stability of this mutant, and the stability of the wild type protein after treatment of cells expressing GRAIL with proteasome inhibitors.

Yeast-two hybrid screening was used in an attempt to isolate GRAIL binding partners to identify a potential pathway for GRAIL-mediated anergy induction. In this screen, several binding partners were identified (Table 1) including a gene encoding an OTU domain that we named DOG because of its phenotype when co-expressed with GRAIL, leading to destabilization of GRAIL expression. OTU domains are found in a variety of proteins, including deubiquitinating enzymes (DUBs) and RNA helicases, but the function of the OTU domain itself has remained elusive. The overall structure of the OTU domain resembles that of the catalytic fold of papain, with a cysteine, an aspartic and a histidine forming the presumed catalytic triad. On two occasions, the otubain-1 protein was captured on an affinity column containing suicide, thiol-reactive ubiquitin-like probes, such as ubiquitin aldehyde or other derivatives. It can also be identified from cell lysates by ubiquitin immunoprecipitation.

Because of its close association with ubiquitin and its cysteine protease like structure, we and others have assayed OTUBAIN-1 (DOG) extensively against several DUB enzyme targets such as linear ubiquitin fusions, polyubiquitinated protein substrates and isolated, branched polyubiquitin chains. Only isolated, branched polyubiquitin chains serve as a substrate for DOG in vitro. This exquisite specificity is usually found in DUBs associated with the proteasome where they carry out ubiquitin recycling functions after removal of the polyubiquitin chain from protein substrates by other DUBs. However, a deubiquitinating function for DOG to destabilize ubiquitinated GRAIL is inconsistent with our results showing that the level of free ubiquitin did not change in cells expressing a catalytically inactive DOG (C91A) despite the overwhelming dominant negative effect on protein ubiquitination demonstrated by C91A when co-expressed with endogenous DOG and GRAIL. Alternatively we considered the possibility that DOG might function as a specific receptor for ubiquitinated GRAIL in association with the proteasome where its over-expression might cause accelerated clearance of ubiquitinated GRAIL. This also turned out to be inconsistent with the results presented above that demonstrate extensive accumulation of non-ubiquitinated GRAIL in the presence of the catalytically inactive C91A mutant of DOG.

In a recent study in which DOG was pulled-down with DUB-specific probes, DOG was isolated by direct association with the probe, but also indirectly, via association with an unidentified DUB. We have demonstrated above that USP8 (UBPy) (Gnesutta et al. (2001) *J Biol Chem*, 276, 39448-39454) is the DOG binding DUB. USP8, DOG and GRAIL form a trimolecular complex in vivo and, unlike DOG, recombinant USP8 was able to de-ubiquitinate polyubiquitinated GRAIL in vitro. Additionally, a catalytically inactive USP8, C748A, bound GRAIL and DOG and caused the accumulation of ubiquitinated GRAIL in cells. In a bacterial co-translational system DOD, but not the catalytically inactive mutant of DOG, C91A, substantially inhibited the proteolytic activity of USP8. Together these data demonstrate that USP8 DUB activity towards ubiquitinated GRAIL may be the ultimate regulator of GRAIL stability and thus the anergy phenotype.

It is possible that DOG functions as an editing protease, allowing the correct growth of polyubiquitin chains, under specific circumstances, a function attributed to a class of enzymes called E4. However, unlike the classical E4 enzymes we were unable to demonstrate E3 ligase-like activity for DOG. Nevertheless, the fact that DOG promoted increased ubiquitination of GRAIL and that the C91A mutant of DOG capped the ubiquitination to a single unit (see FIG. 5E), support this hypothesis.

One interesting aspect of the OTUBAIN-1 (DOG) locus is the generation of multiple transcripts. It appears that most of the transcripts arise not by the use of different transcription initiation or polyadenylation sites, but rather by alternative splicing. We detected at least four transcripts by northern blot analysis of lymphoid organs and were able to isolate two of then with a single pair of PCR primers designed to amplify what was eventually identified as OTUBAIN-1 (DOG). The alternative spliced transcript that we named OTUBAIN-1 ARF-1 (SOG) is missing two thirds of the OTU catalytic domain of DOG, and its translated product may function as a competitor for endogenous DOG. Co-expression of SOG and GRAIL lead to decreased auto-ubiquitination of GRAIL and, as a consequence, increased GRAIL stability, despite the high levels of endogenous DOG in the transfected cells (e.g. T cell hybridomas and HEK 293 cells). Interestingly, while endogenous DOG was present in immunoblots of T cell hybridomas and primary PBMC lysates, endogenous SOG was seen only in T cell hybridoma lysates. Since in both cases SOG RNA was present, the results raise the possibility that this system is controlled by translational regulation, and we are actively investigating the conditions required for differential translation of the diverse RNA products of this locus.

It is also intriguing that the alternative spliced SOG RNA is mostly present in lymphoid organs compared to other solid organs such as liver and brain. This suggests that tissue specific conditions such as pro-inflammatory signals may regulate alternative splicing in this locus. Such a scenario would explain the tissue-specific regulation of endogenous GRAIL protein levels and thus GRAIL activity in inducing the anergy phenotype.

Materials and Methods

Cell lines and plasmids. The ANTC hybridoma T cell line bearing the anti-MBP transgenic TCR was generated and maintained in RPMI-C as previously described. HEK 293-E cells (Invitrogen) were maintained in complete DMEM-GLUTAMAX (10% FCS, 100 ug/ml of penicillin-streptomycin). The P3 IRES GFP retroviral vector is a modification of the pDON-AI plasmid vector (Takara Biosciences) where the SV40-neo cassette of pDON was substituted by the IRES-GFP sequence derived from the pIRES2-GFP plasmid (Clontech, Palo Alto, Calif.) and a new multiple cloning site. P3 IRES-GFP vectors carrying murine wild type GRAIL-V5, the RING finger mutant GRAIL H2N2-V5, the RING domain deletion GRAIL ΔRF-V5, and pET41 (Novagen) GST-GRAILΔTM and GST-GRAILΔTM-H2N2 were generated as described. P3 constructs were used to produce pseudo-typed ecotropic virus in 293 phoenix cells. T cell hybridomas were infected and sorted for GFP bright cells. The pEF6 plasmids carrying DOG or SOG (see below) were linearized and transfected into GRAIL-transduced T cell hybridomas. Clones were selected by limiting dilution in blasticidin-containing medium followed by GFP FACS sorting. Flag-tagged ubiquitin was generated by cloning the human ubiquitin-B gene coding sequence, in frame with the 3×FLAG sequence, in pCMVFLAG 7.1 (Sigma). 293-E and T cell hybridomas were transfected using Lipofectamine 2000 following the manufacturers instructions (Invitrogen).

Northern Blots, PCR and cloning. The sequence of the 525 bp fragment containing a putative GRAIL binding protein was rescued from the yeast two-hybrid assay and blasted against the NCBI human genome database and produced a single hit. The genome scan predicted ORF sequence was used to generate the primers (SEQ ID NO:1) ATGGCGGCG-GAGGAACCTCAGCAG and (SEQ ID NO:2) CTATTTG-TAGAGGATATCGT AGTGTCCCTA. Human tonsil cDNA was used as a template for PCR (Platinum Taq high fidelity, Invitrogen) and the PCR products were cloned by TA cloning into pGEM-Te plasmid vector (Promega, Madison, Wis.) and fully sequenced. HSV (Novagen, San Diego, Calif.) epitope tagged versions of the sequences were produced by PCR with PFU polymerase (Stratagene, San Diego, Calif.) with the primers (SEQ ID NO:3) ctcgagtcaatcctcggggtcttc-cggggcgagttctgcctggctTTTGTA-GAGGATATCGTAGTGTCCCTA and (SEQ ID NO:4) gtc-gactcaatcctcggggtcttccggggcgagttctgcctggctTTTGTAGA GGATATCGTAG TGTCCCTA cloned into either P3 or pEF6 (Invitrogen, Carlsbad, Calif.). His-Xpress epitope tagged versions were produced by subcloning the products from pGEM-Te into pcDNA4 (Invitrogen). The DOG C91A catalytic domain mutant, as well as the R176L and C212A mutants were produced with the Quik-change mutagenesis system (Stratagene). For analysis of differential expression of DOG or SOG in tissues, mRNA from diverse human tissues (Clontech) was treated with DNA-free reagent (Ambion, Austin, Tex.) and subjected to RT-PCR (Superscript one-step RT-PCR, Invitrogen) with the primers: (DOG; SEQ ID NO:5)) CAGCAAGAGATTGCTGTGCAG and (SEQ ID NO:6) CTTGATCTTCTGTTGATAGATGTTGTC; (SOG; SEQ ID NO:7) CGAGTAGGATGTGTCTCGAGTAG and (SEQ ID NO:8) CCAGCATGGGCTCCTCGACCAG. A $^{32}$P labeled DOG anti-sense RNA probe covering the whole coding sequence was synthesized with the T7 Maxi-script kit (Ambion) and used to probe the Immune system 11 multiple tissue northern membrane (Clontech) according to the manufacturer's instructions. Mouse USP8 (UBPy) was cloned by PCR with primers designed from published sequences and fully sequenced. Additional clones were produced by subcloning the USP8 ORF into the pHM6 (HA-Tag) plasmid (Roche Biosciences) and pET28 (Novagen).

Ubiquitination and deubiquitination reactions. For in vitro deubiquitination assays UbB, DOG, DOG-C91A and USP8 were subcloned into the pET28 plasmid (Novagen), expressed from BL21 (DE3) cells and purified in a His affinity column (Pierce). 1 ug of UbB-His was incubated with 100 ng of DOG, DOG-C91A, USP8 or Isopeptidase-T (Calbiochem) at 37 C for 1 hour in DUB buffer (20 mM Tris, 2 mM DTT, 0.5 mM EDTA). Alternatively, synthetic K48-linked tetra-ubiquitin chains (Affiniti Research, U.K) were used in place of UbB. Deubiquitination of substrate-bound polyubiquitin was carried out using autoubiquitinated GST-GRAIL as a substrate. All reaction products were resolved by SDS-PAGE followed by immunoblot. For in vivo deubiquitination assays, pET28-DOG, DOG-C91A, USP8 or empty plasmids were co-transferred into BL21 (DE3) cells along with the pACYC-Duet (Novagen) plasmid carrying a copy of UbB cDNA. Alternatively, pACYC-Duet containing the UbB ORF as well as the DOG or DOG-C91A ORFs were co-transferred along with pET28 USP8. Kanamycin/Chloramphenicol double-resistant colonies were picked and grown in LB media to an A600 of 0.8 and induced with IPTG for 3 hours at 34 C. Cell lysates were produced with BugBuster reagent (Novagen)

and a cocktail of protease inhibitors (Sigma). Cleared lysates were separated by SDS-PAGE and transferred to PVDF for immunoblotting.

Yeast and bacterial two-hybrid analysis. A mouse liver library cloned into pMyr vector was purchased from Stratagene (La Jolla, Calif.). The C-terminal half of Grail, starting at F225, was PCR amplified, cloned into the pSOS vector, and used as bait. Yeast competent cells were co-transformed with either the bait and library or control vectors as described in the CytoTrap instruction manual (Stratagene). More than $5 \times 10^5$ clones were screened. Colonies displaying growth on galactose but not glucose at 37° C. were considered to be putative positives and were used on a secondary screen. Colonies growing in the secondary screen on galactose at 37° C. and in the presence of the GRAIL-SOS bait vector, but not the SOS vector alone were considered true interactors and sequenced. The bacterial-based BacterioMatch two-hybrid system (Stratagene) was used to screen for DOG binding partners. A fusion of full length mouse DOG and λC1 was used as bait to screen $5 \times 10^6$ clones from a mouse liver cDNA library according to instructions. Ampicillin-resistant clones with intense X-Gal staining were isolated and sequenced.

Pull-down assays. Bacterial expressed GST-GRAIL isoforms (2 ug) were incubated with 100,000 c.p.m of $S^{35}$-labeled in-vitro translated DOG and SOG (TNT-T7) (Promega, Madison Wis.). Reactions were rotated for 2 hours at 4° C. and glutathione-agarose beads were added for an additional 2 hours. Beads were collected by centrifugation, washed three times in PBS-0.1% NP-40 and boiled for 3 minutes in reducing Laemli sample buffer. Samples were run in a 12% SDS-PAGE and the gel fixed. Detection of radioactive products was captured using a Phospho-imager (Bio-Rad, Hercules, Calif.).

Antibody production, immunoprecipitations and immunoblots. DOG was inserted into pET28a as an NdeI/XhoI fragment and expressed in *E. coli* (Rosetta DE3, Novagen) as a His fusion protein. His-purified DOG was then used to produce rabbit anti-DOG polyclonal antibody (PolyQuick, Zymed). The resulting antibody is specific to DOG and its isoforms, as it does not react to the closely related otubain-2 protein even when over expressed. For immunoprecipitations, cells were lysed in Brij lysis buffer (25 mM Tris, pH 7.6, 150 mM NaCl, 1 mM DTT, 1% (vol/vol) Brij 96V, 0.1% NP-40, 500 uM PMSF, 20 U/ml aprotinin) for 20 minutes on ice and lysates were clarified by centrifugation at 20,000 g for 15 minutes at 4° C. Cleared lysates were immediately frozen at −70° C. or immunoprecipitated with one of four antibodies covalently coupled to agarose: Anti-V5 tag (Sigma), anti-FlagM2 (Sigma), anti-His tag (Santa Cruz) and anti-HA tag (Santa Cruz). For denaturing immunoprecipitations, lysates were prepared as above and SDS was added to 1% and samples were incubated for 30 minutes and then diluted with Brij lysis buffer so that the SDS concentration was less then 0.1%. Immunocomplexes were tumbled overnight at 4° C. and then washed three times with lysis buffer and one time with water. After the last wash the agarose beads were resuspended in Laemli buffer and heated at 95° C. for 5 minutes. Samples were run on SDS-PAGE gels and transferred to PVDF membranes for immunoblot analysis.

Bone Marrow Chimeras: Retroviral transduction of bone marrow cells was done as previously described with the following modifications (Zhang et al. (1998) Cell, 92, 725-734). P3 constructs were used and retrovirus was generated as described (Anandasabapathy et al., 2003, supra.) After transduction, cells were sorted for GFP expression and infused into BALB/c mice that had received 800 rads of whole body irradiation.

T cell stimulation and IL-2 assay: Single cell suspensions were made from lymph node and spleen cells and CD4+ T cells were positively selected using magnetic beads (Macs). GFP+ cells were then FACS sorted and cultured in complete RPMI (10% heat-inactivated FCS, 10 mM Hepes, 1% non-essential amino acids, 1 mM sodium pyruvate, 100 U/ml penicillin+100 µg/ml streptomycin, 2 mM L-glutamine and 50 µM 2-ME). Cells were cultured in 96 well flat bottom plates at a concentration of $5 \times 10^4$/well. Purified OVA was added at the stated concentrations along with irradiated BALB/c splenocytes (as a source of antigen presenting cells) and supernatant was removed from cultures at 24 hours and assayed immediately for IL-2 or stored at −20° C. Cells from ANTC lines were counted and seeded at a density of $8 \times 10^5$ cells/mL 48 hours prior to use in a T75 tissue culture flask. Forty-eight hours later cells were washed, counted, and seeded at a density of $1 \times 10^6$ cells/mL in RPMI-C into a six well plate with (stimulated) or without (unstimulated) the addition of 1 ug/mL PMA plus 1 ug/mL Ionomycin and supernatants were harvested at 6 hours. Europium Sandwich ELISA (Wallac Inc.) was performed in triplicate wells in 96 well plates using primary rat anti-mouse, and secondary biotinylated anti-mouse antibodies (BD PharMingen), and Europium/streptavidin (Wallac). IL-2 levels were quantified against a standard curve generated from known concentrations of purified recombinant murine IL-2.

Example 2

GRAIL Ubiquitinates a Component of a Multimolecular Complex that Includes Ras-GRF1

As DOG associates with, but is not itself ubiquitinated by GRAIL, other DOG associated proteins are potential substrates. To search for DOG interacting proteins, a bacterial two-hybrid system (BacterioMatch, Stratagene) that can screen large number of clones in a short period of time was used. Using full length DOG fused to the phage λcI as bait we screened a mouse liver library for putative interacting proteins. Positive clones were cloned and sub-cloned into one of many mammalian expression vectors containing epitope tags to use in co-precipitation assays in transfected cell lines. This assay reveals true interactions in a more physiological setting. Three out of four positive clones rescued in the two-hybrid assay co-precipitated with DOG in co-transfection experiments in HEK 293 cells. Notably, a deubiquitinating enzyme, USP8, also called UBPy interacts at high stoichiometry with DOG.

A known substrate for USP8 is ubiquitinated Ras-GFR1. Ras-GRF1 is ubiquitinated after it activates Ras, possibly contributing for the termination of Ras signaling. The E3 ligase responsible for Ras-GRF1 ubiquitination is not known. To test whether GRAIL co-exists with DOG and USP8 in a complex, we co-transfected 293 cells with plasmids coding for GRAIL, USP8 and DOG or a control plasmid for LacZ. After immunoprecipitating cell lysates with an antibody to tagged USP8, we found that both DOG and GRAIL co-precipitate with USP8. This interaction depends on binding of DOG to the catalytic domain of USP8 as c-terminal truncation of USP8 that excluded the catalytic domain did not co-precipitate GRAIL.

Since 293 cells express large amounts of endogenous DOG, we co-transfected these cells with plasmids encoding for GRAIL, USP8 and Ras-GRF1. Again immunoprecipitation of USP8 was able to co-precipitate GRAIL and Ras-GRF1. Finally, to test whether GRAIL plays any role in ubiquitinating the USP8 complex, 293 cells were co-transfected with GRAIL, USP8 and a Flag tagged form of ubiquitin. As a control, a catalytically inactive form of GRAIL, H2N2 was used. Also, we used GRAIL co-expressed with the F-box protein SKP2 and ubiquitin as an additional control for specificity.

Remarkably, GRAIL mediates the ubiquitination of a component of the USP8 complex. Ubiquitination requires the RING domain of GRAIL and does not occur in cells transfected with skp2 instead of USP8.

293 cells were co-transfected with HA-tagged USP8 and DOG-His plasmids, or HA-tagged LacZ as a control. 48 hours after transfection cell lysates were prepared and immunoprecipitated with an anti-HA antibody. Immunocomplexes were resolved by SDS-PAGE, transferred to PVDF and immunoblotted with either anti-His or anti-HA antibodies. 293 cells were co-transfected with HA-USP8, GRAIL-V5 and DOG-His or a c-terminal truncation of USP8 (HA-Rhod). Samples were treated as in "A" and immunoblotted sequentially with anti-V5, anti-His and anti-HA. 293 cells were co-transfected with HA-USP8, GRAIL-V5 and Ras-GRF1-Myc or a c-terminal truncation of USP8 (HA-Rhod). 48 hours after transfection cell lysates were prepared and immunoprecipitated with an anti-antibody. Samples were treated as above, and immunoblotted sequentially with anti-V5 and anti-Myc antibodies. 293 cells were co-transfected with GRAIL-V5, HA-USP8 and a Flag tagged form of ubiquitin. As a control HA-USP8 was substituted with a Glu-Glu version of SKP2 and a catalytically inactive version of GRAIL (H2N2) was used instead of GRAIL. 48 hours after transfection cell lysates were prepared and immunoprecipitated with an anti-HA antibody. Samples were immunoblotted with an anti-Flag antibody to reveal ubiquitination.

Example 3

Constitutive Expression of GRAIL in Naïve CD4+ T Cells is Sufficient to Inhibit Cell Proliferation and IL-2 Production Bone marrow chimeras were used to evaluate functional gene expression in the immune system. These have clinical significance, because bone marrow or hematopoietic stem cell transplantation is a potential treatment for autoimmune disease. Bone marrow cells from D011.10 TCR transgenic mice (reactive towards $OVA_{323-339}$ peptide) were transduced with a retroviral vector expressing wild-type GRAIL (WT), the E3 ligase-inactive form of GRAIL (H2N2), or the retroviral vector expressing GFP only (P3) and injected into lethally irradiated BALB/c syngeneic mice. FACS analysis prior to transfer into lethally irradiated donors demonstrated transduction of long-term multipotent progenitors (Sca-1+, c-kit+, lin−) with wild type GRAIL and H2N2 GRAIL containing vectors, additionally, GFP+ short-lived cells (i.e. neutrophils) were found as far out as 150 days after transplant. The retroviral constructs contained GFP downstream of an IRES sequence and the gene of interest. Constitutive expression of the transgene was tracked using GFP expression as a marker.

GFP expression correlated with expression of the gene of interest and this was reconfirmed with real time QPCR in the bone marrow chimeric mice. Analysis of the CD4+ T cell lineage in reconstituted mice demonstrated that mature CD4+ single positive (SP) T cells developed in the thymus of wild type GRAIL, H2N2 GRAIL and control mice. The phenotype of mature CD4+SP T cells demonstrated equivalent levels of TCR in wild type GRAIL, H2N2 GRAIL and controls.

Lymph node and spleen CD4+ cells from WT GRAIL, H2N2 GRAIL and control-reconstituted mice were sorted for GFP and stimulated in vitro with irradiated splenocytes from unmanipulated BALB/c mice and OVA. Constitutive GRAIL expression in naïve CD4+ T cells resulted in decreased proliferation and IL-2 production. As expected expression of the E3 ligase-inactive form of GRAIL, H2N2 GRAIL, had no effect on the ability of the T cells to proliferate or produce IL-2. These data indicate that constitutive expression of GRAIL with an intact RING domain in naïve CD4+ T cells was sufficient to convey the anergic phenotype.

CD4+T cells were sorted from lymph node and spleen of lethally irradiated BALB/c mice reconstituted with D011.10 bone marrow cells transduced with wild type GRAIL+GFP (WT), H2N2 GRAIL+GFP (H2N2), or mock transduction (D011). 6,000 sorted cells were cultured with $5 \times 10^5$ irradiated BALB/c splenocytes with OVA323-339 peptide (+OVA) or no antigen. Samples were pulsed with 1 mCi 3H-thymidine at 72 hours.

Constitutive expression of WT GRAIL in T cells hybridomas resulted in diminished production of IL-2 at the transcription level after activation with anti-CD3. This effect was not observed with constitutive expression of H2N2 GRAIL, demonstrating that the E3 ligase activity of GRAIL is required to render CD4+T cells anergic. In addition, co-expression of wild-type GRAIL and the H2N2 mutant resulted in a substantial decrease in polyubiquitinated targets in 293 cells suggesting a dominant negative effect.

Based on these observations, it was reasoned that the H2N2 form of GRAIL would act as a dominant negative GRAIL in naïve T cells. To study the role of GRAIL in the induction of anergy in vivo, $1.5 \times 10^6$ CD4+ KJ1.26+ transduced cells from reconstituted H2N2 and P3 mice or unmanipulated D011.10 mice were transferred to unirradiated BALB/c mice in equal numbers. The following day a subset of the mice were immunized. Eight days following transfer and immunization, lymph node and spleen were removed for in vitro proliferation assay. Adoptive transfer of control D011.10 T cells resulted in diminished proliferation in a dose response fashion after administration of iv soluble OVA. Whereas, addition of LPS to the immunization regimen resulted in a productive immune response with a higher proliferative capacity compared to naïve D011.10 T cells. Tolerizing immunization to the P3 expressing T cell recipients demonstrated diminished proliferation compared to naïve and primed D011.10 T cells with a profile that mirrors that seen in the tolerized D011.10 T cells. In sharp contrast, delivery of a tolerizing immunization to the H2N2 expressing T cell recipients demonstrated a blockade in the ability of these cells to be anergized. The proliferative capacity of these cells was comparable to the OVA+LPS immunized D011.10 recipient. Furthermore, in addition to equivalent proliferation between the primed cells and the attempted tolerization of the H2N2 expressing cells, IL-2 production is equivalent as well. There is almost no detectable production of IL-2 in the D011 control cells and P3 expressing cells after a tolerizing immunization consistent with an anergic phenotype.

$1.5-2 \times 10^6$ CD4+KJ1.26+ cells were transferred to unirradiated, syngeneic BALB/c mice intravenously from: D011.10 TCR transgenic mice (D011), lethally irradiated BALB/c mice reconstituted with bone marrow cells transduced with H2N2 GRAIL+GFP (H2) or GFP only (P3). Spleen and lymph node tissue (cervical, axillary, brachial, and inguinal) was removed and pooled for proliferation assay and IL-2 production eight days after immunization.

Bone marrow, containing hematopoietic stem cells from D011.110 TCR transgenic mice, was transduced with retrovirus and transferred into lethally irradiated BALB/c syngeneic mice. FACS analysis prior to transfer into lethally irradiated donors demonstrated transduction of long-term multipotent progenitors with DOG, SOG retrovirus and controls (Sca-1+, c-kit+, lin−). Analysis of the CD4+ T cell lineage in reconstituted mice demonstrated normal development in the thymus of either DOG or SOG T cells as compared to GFP control cells. Lymph node and spleen CD4+ cells from DOG, SOG and control reconstituted mice were sorted for GFP and stimulated in vitro with irradiated splenocytes from normal BALB/c mice and OVA peptide. Constitutive DOG expression in naïve CD4+ T cells resulted in increased IL-2 production, while expression of SOG resulted in almost no IL-2 production. Despite the overall low levels of GRAIL, immunoblot analysis of the purified CD4+ T cells shows further down regulation of endogenous GRAIL levels in DOG T cells and upregulation in SOG cells, just as seen in the co-expression system in T cell hybridomas. These data demonstrate that the balance of DOG and SOG expression in T cells is an important factor regulating GRAIL levels and therefore the outcome of immune responses in secondary lymphoid organs.

D011.10 bone marrow was transduced with retrovirus encoding DOG, SOG or GFP alone and sorted for GFP expression prior to infusion into lethally irradiated BALB/c recipients. After engraftment (5-8 weeks), spleen and lymph node tissues were removed and CD4+ T cells purified by positive selection with magnetic beads. CD4+ T cell suspensions were prepared and stimulated with OVA peptide using irradiated splenocytes from normal BABLB/c mice. Supernatants were collected and measured for IL-2 content by ELISA.

Example 4

Screening for GRAIL Substrates by Protein Interaction

To demonstrate that Ras-GRF1 is a GRAIL substrate, 293 cells are transfected with wild-type GRAIL, the enzymatically inactive RING finger mutant GRAIL-H2N2 along with USP8 and Ras-GRF1. 293 cells have high endogenous levels of DOG (Destabilizer Of GRAIL) protein that recruits the USP8-Ras-GRF-1 complex to GRAIL. 48 hours after transfection cells are lysed and immunoprecipitated with anti-Ras-GRF1 antibody. Immunocomplexes are resolved by SDS-PAGE and transferred to PVDF membranes. The membranes are blotted with anti-ubiquitin antibodies.

Ras-GRF1 has a very close homologue, Ras-GRF2, that is also ubiquitinated. In the case of Ras-GRF2, ubiquitination only takes place after it binds to Ras so that the overall fraction of Ras-GRF2 targeted for degradation after ubiquitination is small. Therefore it is important to test GRAIL-dependent Ras-GRF1 ubiquitination functionally as degradation of Ras-GRF terminates Ras activation, which can be precisely determined by one of several methods.

Since Ras-GRF is primarily activated by calcium signaling, the NIH 3T3 cell line is employed, which has a wild-type Ras allele and can be effectively arrested by serum deprivation, which will lower the basal level of Ras activation to a minimum. We have recently developed 3T3 lines stably expressing a single copy of GRAIL. The GRAIL-3T3 cell line is transfected with the plasmid pDUO (Invitrogen) that has two independent transcriptional units in addition to the drug selectable marker Zeocin. A copy of both USP8 and Ras-GRF1 is inserted in the transcriptional units. After transfection Zeocin-resistant clones are selected and tested for expression of all, GRAIL, USP8 and Ras-GRF1. 3T3 cells already have high endogenous levels of DOG. Control cell lines are produced that lack one of the constructs, GRAIL, USP8 or Ras-GRF1. Cells are seeded at low confluency (~25%) and incubated for 6 hours in complete medium with 10% FCS. The medium is then replaced with low serum media (0.5% FCS) and the cells incubated overnight.

To initiate the experiment, cells are treated with 1 μg/ml of the calcium ionophore: ionomycin to activate Ras via Ras-GRF1 and the kinetics of Ras activation are followed. To this end, cells are lysed in 1% Triton 100 detergent in buffer containing high magnesium, a condition that inhibits the intrinsic GTPase activity of Ras. To determine the content of active Ras (Ras-GTP) the lysates are incubated with a recombinant fusion protein that contains the Ras-binding domain of RAF-1 (a specific Ras effector) fused to GST. RAF-RBD-GST is routinely used to measure Ras activation since it can only bind active Ras. The protein complexes are then captured by glutathione agarose beads, washed extensively and assayed for the presence of Ras by immunoblot with a Ras-specific antibody.

Example 5

Genetic Screening for GRAIL Substrates

E3 ubiquitin ligases promote ubiquitin dependent degradation of their substrates, thus a positive selection genetic screen that relies on GRAIL-mediated ubiquitination as a conditional event for cell survival will identify the substrate(s) of GRAIL.

There is no conventional method for the determination of RING finger E3 ligase substrates. Proteomic efforts are hampered by the fact that ubiquitination is a "ubiquitous" reaction in the cell, resulting in very high background levels. Genetic screens in association with biochemical data have historically allowed powerful insights into the inner workings of cellular physiology. Since E3 ubiquitin ligases promote ubiquitin dependent degradation of their substrates, a positive selection genetic screen is constructed that relies on GRAIL-mediated ubiquitination as a conditional event for cell survival. This screen is applicable to the identification of substrates for any E3 ligase whose substrates are destined for degradation.

A positive selection system is based on GRAIL-mediated ubiquitination and target degradation as a conditional event for cell survival under drug selection. The system is based on a thymidine kinase negative variant of the mouse fibroblast cell line L929 (ATCC). These cells were retrofitted with a composite CMV-based tetracycline inducible promoter construct (TREX, Invitrogen) containing a full length GRAIL insert so that GRAIL expression can be induced with tetracycline. The construct also carries a Zeocin selectable cassette. A clone (5-6-TO) was selected in which basal expression of GRAIL is negligible but can be maximally induced by tetracycline. A copy of the Herpes simplex thymidine kinase open reading frame (HSVTK) minus the stop codon was cloned in the PRJ3 retroviral vector, which is derived from the P3 vector.

Since GRAIL is constitutively expressed in hepatic tissue, a liver cDNA library was fused in the c-terminus of HSVTK, into the PRJ3 vector. We used a 293 based packaging cell line (GPXL) which carries a Maloney virus derived GAG-POL construct and produces, upon co-transfection of the HSVTK retroviral vector based library and the VSVG envelop construct, VSVG pseudo typed virus. After infection of the 54-TO line, cells containing an integrated copy of the virus are selected on HAT medium since the parental line is TK negative. Surviving cells are then treated with tetracycline to induce GRAIL expression followed by gancyclovir. If a substrate is correctly expressed in frame with HSVTK, GRAIL mediated ubiquitination of the fusion protein will induce its degradation and therefore promote cell survival in the presence of the pro-drug.

The insert conferring resistance to gancyclovir is rescued by PCR using HSVTK and virus specific primers, and identified by sequence. The effect of a candidate gene on the development of T cell anergy in vivo is tested by retroviral transduction of bone marrow cells with the candidate gene and reconstitution of lethally irradiated mice.

This technique is used to assess the role of genes rescued from the screens. Bone marrow cells from the OVA 323-339 peptide specific TCR transgenic mice DO11.10 are transduced with a Maloney-based retrovirus carrying a copy of the desired gene in a cassette linked to the GFP gene via an internal ribosome entry site (IRES). GFP positive cells are sorted and analyzed for the presence of long-term hematopoietic stem cells. Positive groups are injected into lethally irradiated BALB/c mice and reconstitution levels are analyzed each week by FACS using blood from the tail vein. After engraftment, lymph node and spleens are removed and CD4+ T cells purified by negative selection using a cocktail of magnetic beads (anti-CD8, anti-B220, anti-MHC class II). Purified cells are then injected into either BALB/Rag$^{-/-}$ mice or sub-lethally irradiated normal BALB/c mice. One week after transfer the mice are challenged with OVA peptide in a stimulatory (peptide+LPS) or tolerogenic (peptide in PBS) form and 8 days after challenge, lymph node and spleen cells are tested for proliferation and IL-2 secretion after restimulation in vitro with irradiated APC and peptide.

In a modification of the method, a modified version of a commercially available lentivirus system (Lentipower, Invitrogen) is used. Because of safety constraints, HIV-based vectors contain a self-inactivating 3'LTR due to a truncation in the U3 region. When the cDNA based vector is copied into the pro-virus genome the truncated 3' LTR is copied into the 5' position effectively inactivating the promoter. For this reason expression in this vector system has to be driven from an internal heterologous promoter. In the original commercial vector (pLenti6) the internal promoter driving the expression of the gene of interest is CMV, while a separate SV40 promoter drives the expression of a Blasticidin-resistance gene. The CMV promoter was replaced with a composite promoter based on the CD45 core promoter and an SV40 enhancer. The SV40-Blasticidin cassette was substituted with an IRES-GFP cassette to allow selection by FACS. Because CD45 is constitutively expressed at high levels in hematopoietic cells, a higher, stable expression of the gene of interest is achieved throughout the hematopoietic compartment.

Example 6

Expression of GRAIL or its Associated Protein-Binding Partners (DOD or SOG) in Human Diseases, Including Cancer and Autoimmunity Cancer. Given the dominant role of GRAIL in limiting cellular proliferation and the tight regulation of GRAIL protein level by DOG, tissues with high expression of DOG should have low levels of GRAIL protein expression, and therefore high levels of cellular proliferation. Normal human peripheral blood cells, for example, have very high levels of DOG protein but no detectable level of GRAIL protein despite readily detectable levels of GRAIL mRNA. A preliminary analysis of DOG expression at the RNA level using a commercially available membrane array, spotted with matched pairs of normal and cancerous tissues from several types of human cancer, revealed a consistently high expression of DOG in most normal and cancerous tissues. However on two occasions, in renal cell carcinoma (stage II and above) and in prostate cancer before involvement of the capsule, DOG expression was significantly down regulated.

Because RNA expression correlates well with protein expression for DOG but not for GRAIL, analyses of protein expression for both DOG and GRAIL in tumor samples are performed in cancer tissue western blot analyses using a two-color fluorescence-based immunoblot scheme, or a more conventional immunofluorescent histopathological analysis of tumor samples stored as paraffin fixed section Human tumor cell lines obtained are used to generate whole cell lysates (e.g., cell will be treated with lysis buffer (1% Brij 96V, 0.1% NP40, 25 mM Tris, pH7.6, 150 mM NaCl and protease inhibitors) for 30 minutes on ice and clear supernatant obtained by a 10 minute centrifugation at 15,000 g. Protein content will be measured by the Bradford method and 200 g of protein per sample will be applied to an individual well of a Dot-Blot apparatus (Pharmacia) fitted with a nitrocellulose membrane. Protein is transferred to nitrocellulose via vacuum filtration. Mouse tumor cell lines are prepared in the same manner. Membranes are blocked with a 1% solution of alkali hydrolyzed specific casein (Novagen) and incubated with a monoclonal antibody specific to GRAIL (anti-GRAIL rat monoclonal antibody reacts with both mouse and human GRAIL) and a rabbit-derived polyclonal antibody specific to DOG (both mouse and human-reactive). After extensive washing, the membranes are incubated with a combination of the secondary antibodies, HRP-labeled goat anti-mouse and Amplex Gold substrate and AP-labeled goat-anti-rabbit and DDAO phosphate substrate (DyeChrome Double Western Blot Stain Kit, Molecular Probes). Following extensive wash, membranes are exposed to a epi-UV illumination source (Licor) and analyzed for the degree of red and green fluorescence for each individual spot, representing each individual sample. The ratio between the colors gives an absolute estimate of the corresponding levels of GRAIL and DOG protein.

Once the pattern of expression is characterized, individual cell lines are tested in vivo in athymic nude mice in an attempt to determine whether expression of DOG or GRAIL are important elements defining the rate of tumor growth. For that purpose, cells expressing low levels of GRAIL or DOG protein are retrovirally transduced with a GRAIL or DOG construct linked to a puromycin-resistant gene via an IRES element. Transduced cells are selected on puromycin for 30 days before injection into nude mice. Groups of five mice are injected subcutaneously with $1\text{-}5\times10^6$ parental or transduced tumor cells in the back and tumor mass is determined every two days by measuring bisecting diameters of the tumor base with vernier calipers. Experiments are repeated at least three times per individual tumor type.

To address the question of GRAIL expression in tumor infiltrating lymphocytes, and whether DOG expression reversibly correlates with GRAIL in this cell type, the TRAMP mouse model of prostate cancer is used. Primary explants of the spontaneous tumor are injected into syngeneic C57/BL6 mice where it grows uniformly. An early passage tumor cell line, pTC1, derived from the TRAMP mice is also used, as it grows unimpeded in syngeneic mice.

An interesting aspect of this tumor model is that there is evidence that appropriate priming conditions for the host T cells can slow tumor growth or eliminate it completely. Forced expression of the costimulatory ligand CD80 on the tumor or injection of a blocking anti-CTLA-4 antibody in the recipient mice can prime the immune system to reject the tumor, suggesting that the tumor is primarily immunogenic but that T cells are rendered anergic by the lack of signal two, for the T cells, or ligation of CTLA-4. It is important to note that ligation of CTLA4 in human CD4+ T cells induces rapid up-regulation of GRAIL.

Groups of C57/BL6 mice are injected subcutaneously with pTC1 cells and collect draining lymph node cells over time in the different groups as tumors grow over 50 mm². Immune-mediated tumor rejection is achieved by the time the tumor mass reaches 50 mm², suggesting lymph node involvement by that stage. T cells are purified from the lymph node by negative selection using magnetic beads labeled antibodies to B cells (B220) and class II positive cells (I-$A^b$). Cell extracts are prepared and analyzed for GRAIL and DOG expression by fluorescent immunoblot as above. Since high levels of DOG expression are expected to decrease GRAIL expression and facilitate T cell responses, and low levels of DOG expression allow the opposite to happen, the direct role of DOG and GRAIL over expression on the rate of tumor growth will be tested using the bone marrow chimera model described above, and incorporating the experimental settings described in the literature that allow for tumor rejection. To attest to the unique role of GRAIL in the process, the H2N2 GRAIL mutant will be used as a negative control, as it possess dominant negative function with regards to T cell tolerance.

Bone marrow derived from normal C57/BL6 mice is used as a source of LT-HSC for lentivirus transduction with GRAIL, DOG and H2N2 constructs as described above. Lethally irradiated recipient mice will be reconstituted with donor bone marrow cells containing transduced LT-HSC. After 5 weeks of reconstitution, mice will be injected with either parental pTC1 cells or CD80-transduced pTC1 cells and disease progress measured as described above. In a separate group of reconstituted mice, anti-CTLA-4 or control antibody injections is performed as described.

Autoimmunity

The levels of DOG and GRAIL RNA were analyzed in the peripheral blood of a number of patients with several autoimmune disorders. While DOG expression was uniformly high, GRAIL expression was variable, equal to healthy donors in multiple sclerosis and rheumatoid arthritis patients, but very low in SLE patients. The fact that GRAIL levels in SLE patients are low in general suggests that it may be an important element in disease development and justify the use of animal models of Lupus as a framework for the evaluation of the genetic programs in autoantigen specific T cells.

In the murine T cell compartment, GRAIL is expressed primarily in anergic cells. Protein expression can be demonstrated exclusively in T cell anergy models in vitro and in vivo. In normal mice, regulatory CD25+ T cells are anergic and express high levels of GRAIL protein. An anergy reporter strain of mice is constructed by homologous recombination of a reporter gene linked in tandem with GRAIL.

A clone containing the entire GRAIL gene (~60 Kb) was chosen as a template for the construction of the knock-in replacement vector, using an internal ribosome entry site (IRES) from the encephalomyocarditis virus, driving the translation of the reporter protein, Green Fluorescent Protein (GFP). For this construct, the coding region of GFP is cloned downstream of an IRES element and targeted to the 3' untranslated region of the GRAIL locus. Because GRAIL may be expressed poorly in ES cells, a Neomycin selection cassette is included in the intron between exons 7 and 8. The Neo cassette is driven by the TK promoter and contains a poly (A) site downstream of Neo and is flanked by two unidirectional LoxP sites for Cre-mediated excision in ES cells. The vector also contains an HSVTK cassette for negative selection. ES cell electroporation and selection are performed at the UCSF transgenic facility.

Screening of Neo-resistant clones is performed primarily by PCR using primers annealing to sequences with intron 7-8, not included in the replacement vector, and Neo specific primers. The "anergy reporter" strain is tested in two animal models of human disease, the NZB×W for SLE and NOD.BDC2.5 for type 1 diabetes. The targeted founder mice are also backcrossed with DO11.10 mice to be used to test the in vivo soluble antigen anergy model.

It has been proposed that the first checkpoint in Lupus development is the loss of tolerance to nuclear antigens in the B cell compartment, followed by loss of tolerance in the T cell compartment, resulting in B cell help and consequent "immune amplification". Groups of "lupus" mice (N=10) are sacrificed every thirty days during a 12-month interval. Lymph nodes and spleens are removed and single cell suspensions analyzed for the presence of GFP+CD4+ T cells, indicative of anergy. Evaluation of renal disease and collection of tissue for histopathological examination is performed using standard techniques. This allows direct correlation of GRAIL expression and disease development, in vivo experiments to investigate the role of genetically dominant isoforms of GRAIL in disease development.

In lupus-prone strains of mice, there are several loci responsible for disease development that have been mapped to Chr 1, 4, 7 and 17. There are also several loci that suppress disease development. In humans, the polygenic nature of Lupus may be even more accentuated. Despite the enormous progress in the genetic dissection of Lupus, no particular gene within these loci has been unambiguously identified. Given the fact that epistatic interactions among these loci are known to play a central role in controlling disease progression, some of these loci may impinge upon GRAIL as regulators of gene expression.

In a second disease model, the reporter strain is backcrossed into NOD.BDC2.5 mice, which carry a transgenic T cell receptor, BDC2.5, with specificity towards a pancreatic antigen. Because of the complicated polygenic nature of the NOD spontaneous diabetes, backcrossing of the BDC2.5 mice into NOD resulted in a mouse (NOD.BDC2.5) in which the disease has very low penetrance. However NOD.BDC2.5 T cells are fully diabetogenic in the NOD.scid mice, upon adoptive transfer.

NOD.BDC2.5-GRAIL-GFP mice are generated, and adoptively transferred T cells from these mice are put into NOD.scid mice. Disease progression is followed by urine analysis for glucose and confirmative blood glucose testing as performed routinely. Groups of mice (N=10) are sacrificed every month and T cells from secondary lymphoid organs as well as from islet infiltrates are purified and segregated into GFP+ (anergic) and GFP-(activated or naïve). GFP-cells are further separated into activated or naïve based upon the expression of the activation markers CD62L and CD44/Pgp-1. Changes in gene expression overtime are analyzed by DNA chip array.

In a third model, the reporter strain is backcrossed into DO11.10 transgenic T cell receptor mice. This TCR recognizes the OVA peptide 323-339 in association with Iad. These mice are rendered tolerant by intravenous injection of soluble OVA peptide in the absence of adjuvant. DO11.10-GRAIL-GFP mice are injected with 300 μg of OVA peptide iv or ip with or without LPS as an adjuvant. Groups of 10 mice are sacrificed at days 3, 5, 10, 15, 30 and 45 days, and T cells from secondary lymphoid organs are purified and separated into GFP+ (anergic) and GFP− (naïve or activated). Lungs and livers are perfused as these organs tend to accumulate relatively large amounts of T cells. Pooled GFP+ and GFP− cells are analyzed for their pattern of gene expression using DNA chip array technology.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of determining the substrates of an E3 ligase, the method comprising:
   introducing an E3 ligase coding sequence operably linked to an inducible promoter into a cell, wherein said cell is deficient in a negatively selectable enzyme;
   introducing into a population of said cells a library of vectors comprising sequences encoding said negatively selectable enzyme fused to candidate E3 ligase substrate coding sequences;
   inducing expression of said E3 ligase in the presence of a compound toxic to cells expressing said enzyme;
   wherein cells expressing said enzyme fused to a substrate for said E3 ligase are viable in the presence of said compound.

2. The method according to claim 1, further comprising the step of rescuing said candidate E3 ligase substrate coding sequences.

3. The method according to claim 2, wherein said rescue comprises specific PCR amplification.

4. The method according to claim 1, wherein said negatively selectable enzyme is thymidine kinase.

5. The method according to claim 1, wherein said E3 ligase is GRAIL.

6. The method of claim 1, further comprising confirming a candidate substrate by complementation in a two hybrid assay.

* * * * *

SEQUENCE LISTING

<160> NUMBER OF SEQ ID NOS: 10

<210> SEQ ID NO 1
<211> LENGTH: 24
<212> TYPE: DNA
<213> ORGANISM: H. sapiens

<400> SEQUENCE: 1
atggcggcgg aggaacctca gcag      24

<210> SEQ ID NO 2
<211> LENGTH: 30
<212> TYPE: DNA
<213> ORGANISM: H. sapiens

<400> SEQUENCE: 2
ctatttgtag aggatatcgt agtgtcccta      30

<210> SEQ ID NO 3
<211> LENGTH: 72
<212> TYPE: DNA
<213> ORGANISM: Artificial Sequence
<220> FEATURE:
<223> OTHER INFORMATION: synthetic primer

<400> SEQUENCE: 3
ctcgagtcaa tcctcggggt cttccggggc gagttctgcc tggcttttgt agaggatatc      60
gtagtgtccc ta      72

<210> SEQ ID NO 4
<211> LENGTH: 72
<212> TYPE: DNA
<213> ORGANISM: Artificial Sequence
<220> FEATURE:
<223> OTHER INFORMATION: synthetic primer

<400> SEQUENCE: 4
gtcgactcaa tcctcggggt cttccggggc gagttctgcc tggcttttgt agaggatatc      60
gtagtgtccc ta      72

<210> SEQ ID NO 5
<211> LENGTH: 21
<212> TYPE: DNA
<213> ORGANISM: H. sapiens

<400> SEQUENCE: 5
cagcaagaga ttgctgtgca g      21

<210> SEQ ID NO 6
<211> LENGTH: 27
<212> TYPE: DNA
<213> ORGANISM: H. sapiens

<400> SEQUENCE: 6

```
cttgatcttc tgttgataga tgttgtc                                          27
```

<210> SEQ ID NO 7
<211> LENGTH: 23
<212> TYPE: DNA
<213> ORGANISM: H. sapiens

<400> SEQUENCE: 7

```
cgagtaggat gtgtctcgag tag                                              23
```

<210> SEQ ID NO 8
<211> LENGTH: 22
<212> TYPE: DNA
<213> ORGANISM: H. sapiens

<400> SEQUENCE: 8

```
ccagcatggg ctcctcgacc ag                                               22
```

<210> SEQ ID NO 9
<211> LENGTH: 271
<212> TYPE: PRT
<213> ORGANISM: H. sapiens

<400> SEQUENCE: 9

```
Met Ala Ala Glu Glu Pro Gln Gln Gln Lys Gln Glu Pro Leu Gly Ser
1               5                   10                  15

Asp Ser Glu Gly Val Asn Cys Leu Ala Tyr Asp Glu Ala Ile Met Ala
            20                  25                  30

Gln Gln Asp Arg Ile Gln Gln Glu Ile Ala Val Gln Asn Pro Leu Val
        35                  40                  45

Ser Glu Arg Leu Glu Leu Ser Val Leu Tyr Lys Glu Tyr Ala Glu Asp
    50                  55                  60

Asp Asn Ile Tyr Gln Gln Lys Ile Lys Asp Leu His Lys Lys Tyr Ser
65                  70                  75                  80

Tyr Ile Arg Lys Thr Arg Pro Asp Gly Asn Cys Phe Tyr Arg Ala Phe
                85                  90                  95

Gly Phe Ser His Leu Glu Ala Leu Leu Asp Asp Ser Lys Glu Leu Gln
            100                 105                 110

Arg Phe Lys Ala Val Ser Ala Lys Ser Lys Glu Asp Leu Val Ser Gln
        115                 120                 125

Gly Phe Thr Glu Phe Thr Ile Glu Asp Phe His Asn Thr Phe Met Asp
    130                 135                 140

Leu Ile Glu Gln Val Glu Arg Gln Thr Ser Val Ala Asp Leu Leu Ala
145                 150                 155                 160

Ser Phe Asn Asp Gln Ser Thr Ser Asp Tyr Leu Val Val Tyr Leu Arg
                165                 170                 175

Leu Leu Thr Ser Gly Tyr Leu Gln Arg Glu Ser Lys Phe Phe Glu His
            180                 185                 190

Phe Ile Glu Gly Gly Arg Thr Val Lys Glu Phe Cys Gln Gln Glu Val
        195                 200                 205

Glu Pro Met Cys Lys Glu Ser Asp His Ile His Ile Ala Leu Ala
    210                 215                 220

Gln Ala Leu Ser Val Ser Ile Gln Val Glu Tyr Met Asp Arg Gly Glu
225                 230                 235                 240

Gly Gly Thr Thr Asn Pro His Ile Phe Pro Glu Gly Ser Glu Pro Lys
                245                 250                 255

Val Tyr Leu Leu Tyr Arg Pro Gly His Tyr Asp Ile Leu Tyr Lys
```

-continued

```
                      260                 265                 270

<210> SEQ ID NO 10
<211> LENGTH: 315
<212> TYPE: PRT
<213> ORGANISM: H. sapiens

<400> SEQUENCE: 10

Met Met Lys Pro Ser Trp Leu Ser Arg Thr Glu Phe Ser Lys Arg Leu
1               5                   10                  15

Leu Cys Arg Thr Leu Trp Cys Gln Ser Gly Trp Ser Ser Arg Ser Tyr
            20                  25                  30

Thr Arg Ser Met Leu Lys Met Thr Thr Ser Ile Asn Arg Arg Ser Arg
        35                  40                  45

Thr Ser Thr Lys Ser Thr Arg Thr Ser Ala Arg Pro Gly Leu Thr Ala
    50                  55                  60

Thr Val Ser Ile Gly Leu Ser Asp Ser Pro Thr Trp Arg His Cys Trp
65                  70                  75                  80

Met Thr Ala Arg Ser Cys Ser Gly Glu Lys Gly Gly His Trp Ala Pro
                85                  90                  95

Arg Gln Val Gly Val Tyr Leu Leu Pro Gly Arg Val Gly Cys Val Ser
            100                 105                 110

Ser Arg Val Ser Pro Ser Phe Pro Gly Asp Gly Leu Asp Ser Gly Leu
        115                 120                 125

Ala Arg Arg Gly Ser Ala Val Ser Ala Leu Ala Ser Gly Leu Val Glu
    130                 135                 140

Glu Pro Met Leu Gly Pro Pro Phe His Pro Thr Pro Arg Phe Lys Ala
145                 150                 155                 160

Val Ser Ala Lys Ser Lys Glu Asp Leu Val Ser Gln Gly Phe Thr Glu
                165                 170                 175

Phe Thr Ile Glu Asp Phe His Asn Thr Phe Met Asp Leu Ile Glu Gln
            180                 185                 190

Val Glu Arg Gln Thr Ser Val Ala Asp Leu Leu Ala Ser Phe Asn Asp
        195                 200                 205

Gln Ser Thr Ser Asp Tyr Leu Val Val Tyr Leu Arg Leu Leu Thr Ser
    210                 215                 220

Gly Tyr Leu Gln Arg Glu Ser Lys Phe Phe Glu His Phe Ile Glu Gly
225                 230                 235                 240

Gly Arg Thr Val Lys Glu Phe Cys Gln Gln Val Glu Pro Met Cys
                245                 250                 255

Lys Glu Ser Asp His Ile His Ile Ile Ala Leu Ala Gln Ala Leu Ser
            260                 265                 270

Val Ser Ile Gln Val Glu Tyr Met Asp Arg Gly Glu Gly Gly Thr Thr
        275                 280                 285

Asn Pro His Ile Phe Pro Glu Gly Ser Glu Pro Lys Val Tyr Leu Leu
    290                 295                 300

Tyr Arg Pro Gly His Tyr Asp Ile Leu Tyr Lys
305                 310                 315
```